US009776975B2

(12) United States Patent
Chang et al.

(10) Patent No.: US 9,776,975 B2
(45) Date of Patent: Oct. 3, 2017

(54) QUINAZOLINONE ANTIBIOTICS

(71) Applicant: University of Notre Dame Du Lac, Notre Dame, IN (US)

(72) Inventors: Mayland Chang, Granger, IN (US); Shahriar Mobashery, Granger, IN (US); Renee Bouley, Mishawaka, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/773,603

(22) PCT Filed: Mar. 5, 2014

(86) PCT No.: PCT/US2014/020910
§ 371 (c)(1),
(2) Date: Sep. 8, 2015

(87) PCT Pub. No.: WO2014/138302
PCT Pub. Date: Sep. 12, 2014

(65) Prior Publication Data
US 2016/0031832 A1  Feb. 4, 2016

Related U.S. Application Data

(60) Provisional application No. 61/851,310, filed on Mar. 5, 2013.

(51) Int. Cl.
| | | |
|---|---|---|
| *A61K 31/517* | (2006.01) |
| *C07D 239/91* | (2006.01) |
| *C07D 401/06* | (2006.01) |
| *C07D 405/06* | (2006.01) |
| *C07D 471/04* | (2006.01) |
| *A61K 45/06* | (2006.01) |
| *A61K 31/43* | (2006.01) |
| *A61K 31/431* | (2006.01) |
| *A61K 31/545* | (2006.01) |
| *A61K 31/546* | (2006.01) |
| *A61K 31/7036* | (2006.01) |
| *A61K 31/7048* | (2006.01) |
| *A61K 31/519* | (2006.01) |
| *A61K 31/5377* | (2006.01) |
| *C07D 401/12* | (2006.01) |

(52) U.S. Cl.
CPC ............ *C07D 239/91* (2013.01); *A61K 31/43* (2013.01); *A61K 31/431* (2013.01); *A61K 31/517* (2013.01); *A61K 31/519* (2013.01); *A61K 31/5377* (2013.01); *A61K 31/545* (2013.01); *A61K 31/546* (2013.01); *A61K 31/7036* (2013.01); *A61K 31/7048* (2013.01); *A61K 45/06* (2013.01); *C07D 401/06* (2013.01); *C07D 401/12* (2013.01); *C07D 405/06* (2013.01); *C07D 471/04* (2013.01)

(58) Field of Classification Search
CPC .................................................... C07D 239/91
See application file for complete search history.

(56) References Cited

U.S. PATENT DOCUMENTS 7,893,260 B2 * 2/2011 Chong ................. A61K 31/517
544/287
2010/0004324 A1  1/2010 Skaar et al.
2010/0197650 A1  8/2010 Biek

FOREIGN PATENT DOCUMENTS

| JP | 01110677 | 4/1989 |
| JP | H01-110677 | 4/1989 |
| WO | 2005/120510 A1 | 12/2005 |
| WO | 2005120510 A1 | 12/2005 |
| WO | 2007/056124 A2 | 5/2007 |
| WO | 2007056124 A2 | 5/2007 |
| WO | 2009082398 A1 | 7/2009 |
| WO | 2009/137677 A2 | 11/2009 |
| WO | 2009137677 A2 | 11/2009 |

OTHER PUBLICATIONS

Dabiri, Minoo et al., "Novel and Efficient One-Pot Tandem Synthesis of 2-Styryl-Substituted 4(3H)-Quinazolinones," Journal of Combinatorial Chemistry, 2008, 700-703, 10.
International_Search_Report_App_No. PCT_US2014_020910.
Jantova, Sona et al., "In vitro antibacterial activity of ten series of substituted quinazolines," Biologia, 2004, 741-752, 59.
Jessy, E et al., "Synthesis and biological evaluation of some novel quinazolone derivatives," Indian Journal of Pharmaceutical Sciences, 2007, 476-478, 69.
Khajavi, Mohammad et al., "Reaction of Anthranilic Acid with Orthoesters: a New Facile One-pot Synthesis of 2-Substituted 4H-3,1-Benzoxazin-4-ones," Journal of Chemical Research, 1997, 286-287, 1.
Mosley, Cara A. et al., "Quinazolin-4-one Derivatives: A Novel Class of Noncompetitive NR2C/D Subunit-Selective N-Methyl-D-aspartate Receptor Antagonists," Journal of Medicinal Chemistry, 2010, 5476-5490, 53.

(Continued)

*Primary Examiner* — Brian McDowell
(74) *Attorney, Agent, or Firm* — Haukaas Fortius PLLC; Michael H. Haukaas

(57) ABSTRACT

A new class of antibiotics effective against methicillin-resistant *Staphylococcus aureus* (MRSA) is disclosed. Compounds of this class can impair cell-wall biosynthesis by binding to both the allosteric and the catalytic domains of penicillin-binding protein (PBP) 2a. This class of antibiotics holds promise in reversing obsolescence of staphylococcal PBPs as important targets for antibiotics. Embodiments of the invention thus provide novel antibacterial compounds that target penicillin-binding proteins and/or other important cellular targets. Methods for inhibiting the growth and/or replication of bacteria using the compounds described herein are also provided. Various embodiments exhibit activity against gram positive bacteria, including drug-resistant strains of *Staphylococcus aureus*.

13 Claims, 18 Drawing Sheets

(56) References Cited

OTHER PUBLICATIONS

Murti, Y et al., "New 6-Bromo-2-Methyl-3-(Substituted Phenyl)-(3H)-Quinazolin-4-0nes with Antimicrobial and Antiinflammatory Activities," Indian Journal of Pharmaceutical Sciences, 2011, 333-337, 73.
Written_Opinion_App_No. PCT_US2014_020910.
Kacker et al., "Potential Analgesics. Part I. Synthesis of Substituted 4-Quinazolones", Journal of the Indian Chemical Society, vol. 28, No. 6, 1951, pp. 344-346.
Kozhevnikov et al., "Issledovanie v Ryadu 3H-Khinazolona-4. XI. Sintez i Svoistva 3-[4-Bromfenil]-1, 2, 3, 4-Tetragidrokhininazolinonov-4. Khimiko Farmatsevtichesky Zhurnal", Moskva 'Meditsina', vol. 16, No. 11, 1982, pp. 1349-1353; with English-language version of bibliographic data, 1 pg., translation dated Aug. 14, 2014, by Rospatent, Federal Service for Intellectual Property, FIPS Int'l Searching Authority (Federal Institute of Industrial Property); 6 pgs.
Panneerselvam et al., "Synthesis, Characterization and Biological Activities of Novel 2-Methyl-Quinazolin-4(3H)-Ones", Indian Journal of Pharmaceutical Sciences, vol. 65, No. 3, May 2003, pp. 268-273; Indian Pharmaceutical Association.

\* cited by examiner

| Structure | ID# | Comp ID Log P | S. aureus ATCC 29213 | | E. faecium NCTC 7171 | |
|---|---|---|---|---|---|---|
| | | | MH | MH + BSA | MH | MH + BSA |
| 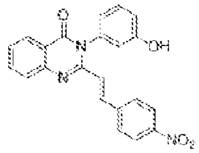 | 1 | 3456-0274 log P 3.92 | 2 | >128 | 32 | 128 |
| 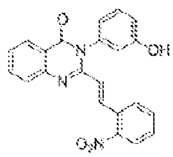 | 2 | 3456-0276 log P 3.92 | 128 | >128 | 64 | 128 |
| 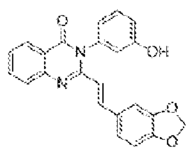 | 3 | 3379-1103 log P 4.50 | 2 | >128 | 32 | >128 |
| 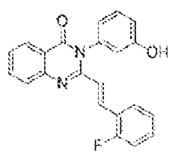 | 4 | 3456-0279 log P 4.88 | 1 | 128 | 32 | 64 |
| 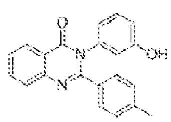 | 5 | 4123-0441 log P 4.87 | 128 | >128 | 128 | >128 |
| 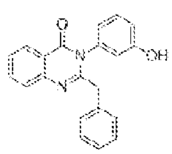 | 6 | 3966-0012 log P 4.33 | 32 | 128 | >128 | >128 |

| | | | | | | |
|---|---|---|---|---|---|---|
|  | 7 | RB-1-126 log P 3.92 | 2 | >128 | 32 | 128 |
|  | 8 | RB-1-142 log P 4.81 | >128 | >128 | >128 | >128 |
|  | 9 | RB-1-113 log P 4.93 | >128 | >128 | 8 | >128 |
|  | 10 | RB-1-135 log P 3.92 | >128 | >128 | 8 | 64 |
|  | 11 | RB-1-131 log P 3.92 | >128 | >128 | 64 | >128 |
|  | 12 | RB-1-066 log P 4.04 | >128 | >128 | 64 | >128 |
|  | 13 | RB-1-076 log P 4.04 | >128 | >128 | 32 | >128 |

| Structure | # | Name / log P | | | | |
|---|---|---|---|---|---|---|
| 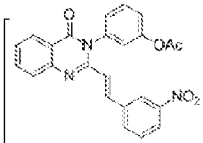 | 14 | RB-1-079 log P 4.04 | >128 | >128 | 64 | >128 |
| 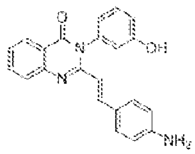 | 15 | RB-1-129 log P 2.93 | 16 | >128 | 32 | >128 |
| 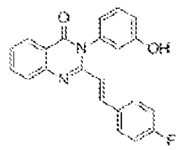 | 16 | RB-1-172 log P 4.88 | 0.25 | 4 | >128 | >128 |
| 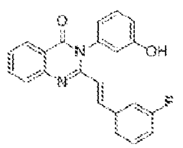 | 17 | RB-1-208 log P 4.88 | 1 | 8 | 128 | >128 |
| 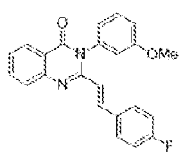 | 18 | RB-1-216 log P 5.14 | >128 | >128 | >128 | >128 |
| 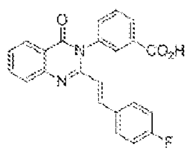 | 19 | RB-1-222 log P 4.83 | 1 | 8 | >128 | >128 |
| 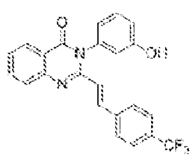 | 20 | RB-1-276 log P 5.54 | 128 | >128 | 16 | 32 |

| | | | | | | |
|---|---|---|---|---|---|---|
|  | 21 | RB-2-001 log P 4.72 | 0.5 | 8 | 64 | 64 |
|  | 22 | RB-2-021 log P 4.49 | 32 | >128 | 32 | 64 |
|  | 23 | RB-2-046 log P 4.44 | >128 | >128 | >128 | >128 |
|  | 24 | RB-2-058 log P 4.47 | 2 | 16 | 128 | >128 |
|  | 25 | RB-2-060 log P 4.18 | 1 | 8 | >128 | >128 |
|  | 26 | RB-2-064 log P 3.49 | 0.125 | 1 | >128 | >128 |
|  | 27 | RB-2-088 log P 5.28 | 0.125 | 1 | 32 | >128 |

| | | # | | | | |
|---|---|---|---|---|---|---|
|  | RB-2-086 log P 3.39 | 28 | 2 | 4 | >128 | >128 |
|  | RB-2-090 log P 4.33 | 29 | >128 | >128 | >128 | >128 |
|  | RB-2-092 log P 4.76 | 30 | 0.03 | 0.125 | 64 | >128 |
|  | RB-2-094 log P 4.60 | 31 | 4 | 32 | >128 | >128 |
|  | RB-2-095 log P 5.21 | 32 | 0.25 | 4 | 32 | >128 |
|  | RB-2-096 log P 3.34 | 33 | 128 | >128 | 128 | >128 |
|  | RB-2-102 log P 4.28 | 34 | >128 | >128 | >128 | >128 |

| | | | | | | |
|---|---|---|---|---|---|---|
|  | 35 | RB-2-108 log P 4.18 | 4 | 8 | >128 | >128 |
|  | 36 | RB-2-116 log P 4.70 | 2 | 8 | >128 | >128 |
|  | 37 | RB-2-117 log P 4.34 | 0.5 | 2 | >128 | >128 |
|  | 38 | RB-2-119 log P 3.37 | 0.004 | 0.03 | >128 | >128 |
|  | 39 | RB-2-120 log P 4.05 | 0.25 | 2 | >128 | >128 |
|  | 40 | RB-2-122 log P 4.64 | 0.5 | 4 | >128 | >128 |
|  | 41 | DR-02-137 log P 3.42 | 0.5 | 4 | 128 | >128 |

| Structure | # | ID | | | | |
|---|---|---|---|---|---|---|
| 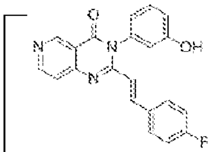 | 42 | DR-02-147 log P 3.54 | 1 | 8 | >128 | >128 |
| 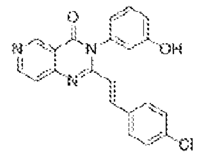 | 43 | DR-02-149 log P 3.94 | 1 | 2 | >128 | >128 |
| 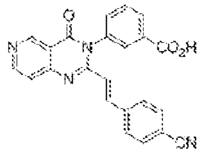 | 44 | DR-02-200 log P 3.37 | >128 | >128 | >128 | >128 |
| 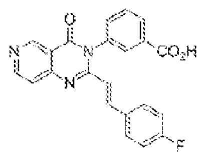 | 45 | DR-02-201 log P 3.49 | 64 | 128 | >128 | >128 |
| 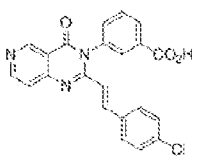 | 46 | DR-02-207 log P 3.89 | 64 | >128 | >128 | >128 |
| 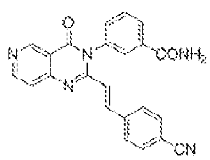 | 47 | DR-02-217 log P 2.72 | >128 | >128 | >128 | >128 |
| 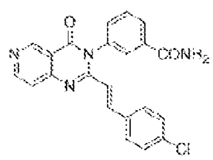 | 48 | DR-02-229 log P 3.24 | >128 | >128 | >128 | >128 |

| | | | | | | |
|---|---|---|---|---|---|---|
| [structure] | 49 | DR-02-235 log P 2.84 | >128 | >128 | >128 | >128 |
| [structure] | 50 | DR-02-236 log P 3.17 | >128 | >128 | >128 | >128 |
| [structure] | 51 | DR-02-254 log P 3.90 | 2 | 64 | >128 | >128 |
| [structure] | 52 | DR-02-262 log P 3.24 | 1 | 4 | >128 | >128 |
| [structure] | 53 | DR-02-280 log P 4.27 | 8 | 128 | >128 | >128 |
| [structure] | 54 | DR-02-283 log P 5.39 | 2 | 64 | >128 | >128 |
| [structure] | 55 | DR-02-284 log P 3.38 | >128 | >128 | >128 | >128 |

*Figure 12 (cont.)*

| | | | | | | |
|---|---|---|---|---|---|---|
| | 56 | DR-02-291 log P 2.16 | >128 | >128 | >128 | >128 |
| | 57 | RB-2-128 clog P 3.6 | 4 | 8 | >128 | >128 |
| | 58 | DR-02-294 log P 4.99 | 2 | 8 | >128 | >128 |
| | 59 | DR-02-299 log P 4.02 | 8 | 16 | >128 | >128 |
| | 60 | DR-03-255 log P 5.04 | 0.06 | 4 | >128 | >128 |
| | 61 | DR-03-281 log P 2.25 | >128 | >128 | >128 | >128 |

*Figure 12 (cont.)*

| | | | | | |
|---|---|---|---|---|---|
|  | 62 | DR-03-285 log P 4.52 | >128 | >128 | 128 | 128 |
|  | 63 | DR-03-299 log P 5.30 | 0.01 | 2 | >128 | >128 |
|  | 64 | DR-04-013 log P 1.84 | >128 | >128 | >128 | >128 |
|  | 65 | DR-04-014 log P 3.58 | 0.015 | 0.25 | >128 | >128 |
|  | 66 | DR-04-042 log P 5.54 | 2 | 8 | >128 | >128 |
|  | 67 | DR-04-045 log P 4.92 | >128 | >128 | >128 | >128 |

| | | | | | |
|---|---|---|---|---|---|
|  | 68 | RB-2-141 log P 3.07 | >128 | >128 | >128 | >128 |
|  | 69 | RB-2-145 log P 3.92 | 2 | 8 | >128 | >128 |
|  | 70 | RB-2-147 log P 4.83 | 0.03 | 0.25 | >128 | >128 |

QUINAZOLINONE ANTIBIOTICS

RELATED APPLICATIONS

This application claims priority under 35 U.S.C. §119(e) to U.S. Provisional Patent Application No. 61/851,310, filed Mar. 5, 2013, which is incorporated herein by reference.

GOVERNMENT SUPPORT

This invention was made with government support under AI090818 and T32GM075762 awarded by the National Institutes of Health. The government has certain rights in the invention.

BACKGROUND OF THE INVENTION

*Staphylococcus aureus* is a common bacterium found in moist areas of the body and skin. *S. aureus* can also grow as a biofilm, representing the leading cause of infection after implantation of medical devices. Approximately 29% (78.9 million) of the US population is colonized in the nose with *S. aureus*, of which 1.5% (4.1 million) is methicillin-resistant *S. aureus* (MRSA). In 2005, 478,000 people in the US were hospitalized with a *S. aureus* infection, of these 278,000 were MRSA infections, resulting in 19,000 deaths. MRSA infections have been increasing from 2% of *S. aureus* infections in intensive care units in 1974 to 64% in 2004, although more recent data report stabilization. Approximately 14 million outpatient visits occur every year in the US for suspected *S. aureus* skin and soft tissue infections. About 76% of these infections are caused by *S. aureus*, of which 78% are due to MRSA, for an overall rate of 59%. Spread of MRSA is not limited to nosocomial (hospital-acquired) infections, as they are also found in community-acquired infections. Over the years, β-lactams were antibiotics of choice in treatment of *S. aureus* infections. However, these agents faced obsolescence with the emergence of MRSA. Presently, vancomycin, daptomycin or linezolid are agents for treatment of MRSA infections, although only linezolid can be dosed orally. Resistance to all three has emerged. Thus, new anti-MRSA therapeutic strategies are needed, especially agents that are orally bioavailable.

Clinical resistance to β-lactam antibiotics by MRSA has its basis predominantly in acquisition of the mecA gene, which encodes penicillin-binding protein 2a (PBP2a). PBP2a, a cell-wall DD-transpeptidase, is refractory to inhibition by essentially all commercially available β-lactams (ceftaroline is an exception), antibiotics that irreversibly acylate the active-site serine of typical PBPs. PBPs catalyze biosynthesis of the bacterial cell wall, which is essential for the survival of the bacterium. Accordingly, new non-β-lactam antibiotics that inhibit PBP2a are needed to combat drug-resistant strains of bacteria.

SUMMARY

*Staphylococcus aureus* is responsible for a number of human diseases, including skin and soft tissue infections. Annually, 292,000 hospitalizations in the US are due to *S. aureus* infections, of which 126,000 are related to methicillin-resistant *Staphylococcus aureus* (MRSA), resulting in 19,000 deaths. A novel structural class of antibiotics has been discovered and is described herein. A lead compound in this class shows high in vitro potency against Gram-positive bacteria comparable to those of linezolid and superior to vancomycin (both considered gold standards) and shows excellent in vivo activity in mouse models of MRSA infection.

The invention thus provides a novel class of non-β-lactam antibiotics, the quinazolinones, which inhibit PBP2a by an unprecedented mechanism of targeting both its allosteric and active sites. This inhibition leads to the impairment of the formation of cell wall in living bacteria. The quinazolinones described herein are effective as anti-MRSA agents both in vitro and in vivo. Furthermore, they exhibit activity against other Gram-positive bacteria. The quinazolinones have anti-MRSA activity by themselves. However, these compounds synergize with β-lactam antibiotics. The use of a combination of a quinazolinone with a β-lactam antibiotic can revive the clinical use of β-lactam antibacterial therapy in treatment of MRSA infections. The invention provides a new class of quinazolinone antibiotics, optionally in combination with other antibacterial agents, for the therapeutic treatment of methicillin-resistant *Staphylococcus aureus* and other bacteria.

Accordingly, the invention provides a compound of Formula (A):

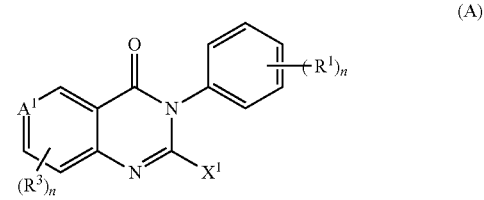

(A)

wherein
$A^1$ is N or $CR^3$ (e.g., CH, or C when $A^1$ is substituted with $R^3$);
each $R^1$ is independently H, hydroxy, halo, trifluoromethyl, alkyl, alkoxy, acyloxy, amino, —$CO_2H$, nitro, nitrile, —$NR^x_2$ wherein each $R^x$ is independently H, alkyl, acyl, benzyl, or alkoxycarbonyl, —$SO_2$—$R^y$ wherein $R^y$ is —OH, —$NH_2$, alkyl or aryl, —NH—$SO_2$—$R^y$ wherein $R^y$ is —OH, alkyl or aryl, —C(=O)$NR^x_2$ wherein each $R^x$ is independently H, alkyl, hydroxyalkyl, cycloalkyl, acyl, picolinyl, or benzyl, —$CH_2$—N(H)$R^4$ wherein $R^4$ is H or acyl, —$CH_2$—$CO_2H$, heterocycle, —$CH_2$-heterocycle, or —C(=NH)$NH_2$;
$X^1$ is ($C_1$-$C_{12}$)alkyl wherein alkyl is optionally substituted with cycloalkyl or heterocycle, ($C_1$-$C_2$)alkyl-Ph-$(R^2)_m$, —C=C-cycloalkyl, —C=C-heterocycle, or —C=C-Ph-$(R^2)_m$, wherein m is 1, 2, 3, 4, or 5;
each $R^2$ is independently H, hydroxy, halo, trifluoromethyl, alkyl, alkoxy, acyloxy, amino, —$CO_2H$, nitro, nitrile, —$SO_2$—$R^y$ wherein $R^y$ is —OH, —$NH_2$, alkyl or aryl, alkenyl, alkynyl, or two $R^2$ groups form a 1,2-dioxolane ring on the phenyl ring to which they are attached;
each $R^3$ is independently H, hydroxy, halo, trifluoromethyl, alkyl, —$CO_2H$, —$CO_2$-alkyl, or —C(=O)$NR^x_2$ wherein each $R^x$ is independently H, alkyl, hydroxyalkyl, acyl, picolinyl, or benzyl; and
each n is independently 1, 2, 3, 4, or 5;
or a pharmaceutically acceptable salt or solvate thereof.

In some embodiments, the compound of Formula (A) is a compound of Formula (I):

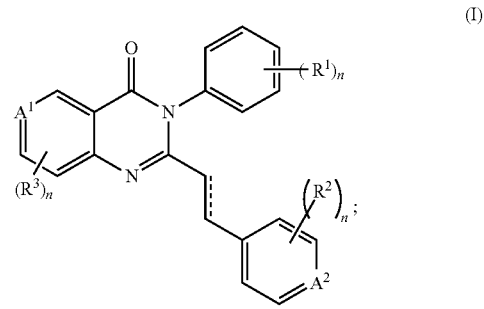

(I)

wherein $A^1$, $R^1$, $R^2$, and $R^3$ are as defined for Formula (A), the n variable of $R^2$ is 1, 2, 3, 4, or 5, $A^2$ is N, $N^+$Me, CH, or C when substituted by $R^2$, and the bond represented by dashes represents an optional double bond; or a pharmaceutically acceptable salt or solvate thereof.

In some embodiments, the compound of Formula (I) is a compound of Formula (II):

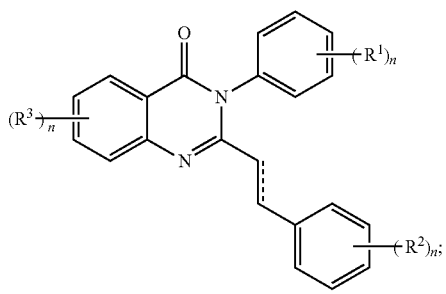

(II)

or a pharmaceutically acceptable salt or solvate thereof.

In some embodiments, the compound of Formula (II) is a compound of Formula (III):

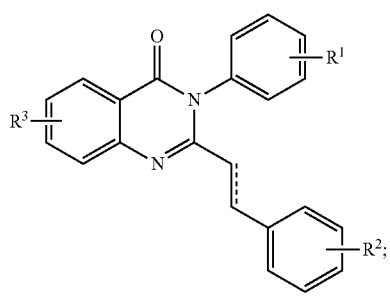

(III)

or a pharmaceutically acceptable salt or solvate thereof.

In some embodiments, the compound of Formula (III) is a compound of Formula (IV):

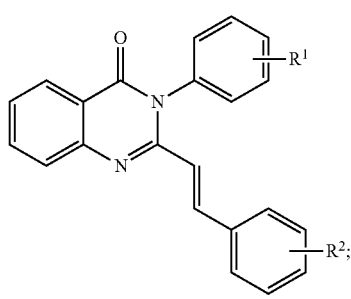

(IV)

or a pharmaceutically acceptable salt or solvate thereof. $R^1$ and $R^2$ can be at any position of the phenyl moiety to which they are attached, in any of Formulas (A) and (I)-(IV). For example, $R^1$ can be specifically ortho, meta, or para to the site of attachment of the phenyl moiety to the remainder of the formula. Likewise, $R^2$ can be specifically ortho, meta, or para to the site of attachment of the phenyl moiety to the remainder of the formula. Thus, the compounds of the invention can have $R^1$ and $R^2$ positional isomers for each of the nine different combinations of the positions of $R^1$ and $R^2$, in various embodiments.

In some embodiments, the compound of Formula (IV) is a compound of Formula (V):

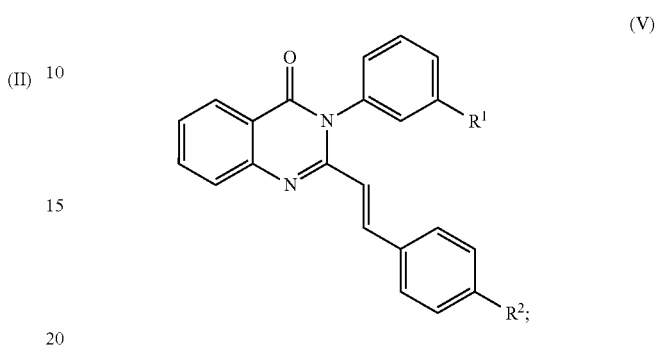

(V)

or a pharmaceutically acceptable salt or solvate thereof.

In each of the formulas above, $R^1$ can be hydroxy, acetoxy, —$CO_2H$, amino, —NH—C(=O)Me, —NH—C(=O)OMe, —NH—$SO_2$Me, —C(=O)$NH_2$, —C(=O)NH($C_1$-$C_8$)alkyl-OH, —C(=O)NH(3-picolinyl) wherein the pyridine moiety of the picolinyl group is optionally substituted with alkyl or alkoxy, —NH($C_1$-$C_8$)alkyl, or —$CH_2$NH—C(=O)Me. In certain specific embodiments, $R^1$ is hydroxy, —$CO_2H$, —NH—C(=O)Me, —NH—$SO_2$Me, —NH—C(=O)OMe, or —C(=O)N(H)$CH_2CH_2$OH. In various embodiments, any one or more of the variables listed for $R^1$, as well as for $R^2$ and $R^3$, can be excluded from the definition of said variable element.

In each of the formulas above, $R^2$ can be H, halo, methyl, methoxy, nitro, nitrile, ethynyl, or two $R^2$ groups form a 1,2-dioxolane ring on the phenyl ring to which they are attached. In certain specific embodiments, $R^2$ is fluoro, chloro, nitro, nitrile, methyl, or ethynyl.

In some embodiments, $R^1$ is located at a position meta to the site of attachment to the quinazoline core of Formula (V).

In various embodiments, $R^2$ is located at a position para to the site of attachment to the ethylene moiety of Formula (V).

In various embodiments, $R^3$ can be halo, such as bromo. $R^3$ can be located at the 5-, 6-, 7-, or 8-position of the quinazolinone of the formulas above.

A compound of a formula above can have a minimum-inhibitory concentrations (MIC) against methicillin-resistant *Staphylococcus aureus* strains of less than 2.5 μg/mL. The ΔMIC in the presence of bovine serum albumin compared to the absence of the bovine serum albumin can be less than or equal to 8 fold.

In certain specific embodiments, a compound of the invention is compound 28, 41, 42, or 43 of FIG. 12. In other specific embodiment, the compound is compound 3, 9, 54, 58, or 59 of FIG. 12. In additional specific embodiments, the compound is compound 1, 4, 7, 10, 16, 17, 19, 21, 24, 25, 26, 27, 30, 31, 32, 35, 36, 37, 38, 39, 40, 51, 52, 53, 57, 63, 65, 66, 67, or 70 of FIG. 12. In further specific embodiments, the compound is a compound illustrated in FIG. 12 or FIG. 13.

The invention also provides a composition comprising a compound described above in combination with a pharmaceutically acceptable carrier, diluent, or excipient. The invention additionally provides a composition comprising a compound described above in combination with a second antibiotic, for example, an antibiotic recited herein.

In another embodiment, the invention provides methods for inhibiting growth of bacteria comprising contacting a bacteria with an effective antibacterial amount of a compound described herein. The bacteria can be on or in a mammal and the compound can be administered orally or intraperitoneally to the mammal. The bacteria can be a gram positive bacteria. In some embodiments, the bacteria comprises at least one strain of *Enterococcus* or *Staphylococcus aureus*. In certain embodiments, the bacteria is a drug-resistant strain of the genus *Staphylococcus*. In certain specific embodiments, the bacteria is a methicillin-resistant *Staphylococcus aureus* (MRSA) strain.

The invention further provides for the use of a compound described herein to prepare a medicament for treatment of a bacterial infection. The bacterial infection can be caused by at least one strain of *Enterococcus* or *Staphylococcus aureus*. The bacterial infection can also be caused by a drug-resistant strain of the genus *Staphylococcus*. In certain specific embodiments, the bacterial infection is caused by a methicillin-resistant *Staphylococcus aureus* (MRSA) strain.

In other embodiments, the invention provides a method of treating an animal inflicted with a bacterial infection by administering to an animal in need of such treatment an effective amount of an antibacterial compound of a formula described herein. In various embodiments, the compound can be in the form of a therapeutic composition, as described herein.

The invention also provides a method of killing or inhibiting (e.g., the growth of) a bacteria comprising contacting the bacteria with an effective amount of a compound of a formula described herein. In one embodiment, the contacting is in vitro. In another embodiment, the contacting is in vivo. The bacteria can be, for example, a gram positive bacteria. Examples of the bacteria include, but are not limited to, *S. aureus, Enterococcus faecalis, Pseudomonas aeruginosa, Klebsiella pneumonia* and *Proteus mirabilis*, as well as vancomycin-resistant methicillin-resistant *Staphylococcus aureus*.

The invention yet further provides methods for opening the active catalytic site of PBP2a to enable synergistic antibacterial activity with other antibiotics including beta-lactams, wherein the method includes contacting a bacteria with an effective amount of a compound described herein, thereby causing the compound to bind to the allosteric site of PBP2a, and thereby opening the active catalytic site of PBP2a, thereby allowing the other antibiotic to effectively kill or inhibit the bacteria that includes the PBP2a. In one embodiment, the other antibiotic (a second antibiotic) is ceftaroline, or an antibiotic recited herein.

The invention thus provides novel compounds of the formulas described herein, intermediates for the synthesis of compounds of the formulas described herein, as well as methods of preparing compounds the formulas described herein. The invention also provides compounds of the formulas described herein that are useful as intermediates for the synthesis of other useful compounds. The invention provides for the use of compounds of the formulas described herein for the manufacture of medicaments useful for the treatment of bacterial infections in a mammal, such as a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

The % inhibition is calculated by comparison to a negative control containing no antibiotic; the maximum inhibition observed is reported.

Figure 9:
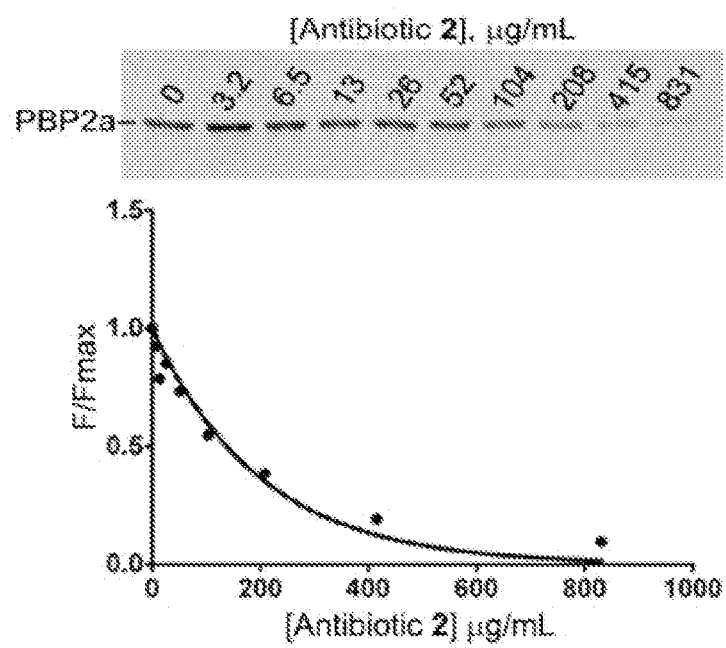

FIG. 9. Determination of the mechanism of action for quinazolinone 2. Fluorescence labeling of recombinant purified PBP2a (1 μM) by Bocillin FL (20 μM) in the presence of increasing amounts of antibiotic 2 (shown in μg/mL). Relative fluorescence intensity of the PBP2a band (where F is the measured fluorescence and Fmax is maximum fluorescence in the absence of antibiotic) is plotted against the concentration of antibiotic 2 (μg/mL).

Figure 10:
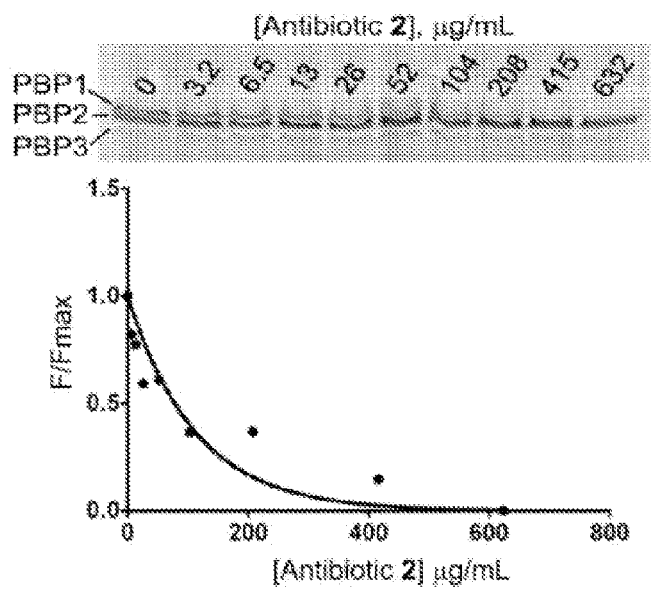

FIG. 10. Determination of the mechanism of action for quinazolinone 2. Fluorescence labeling of S. aureus membrane preparation (150 μg) by Bocillin FL (30 μM) in the presence of increasing amounts of antibiotic 2 (shown in μg/mL). Relative fluorescence intensity of the PBP1 band is plotted against the concentration of antibiotic 2 (μg/mL). Data were fit by nonlinear regression using the published equation,[13] with $R^2$ values of 0.95 and 0.87 for panels c and d, respectively.

Figure 11:
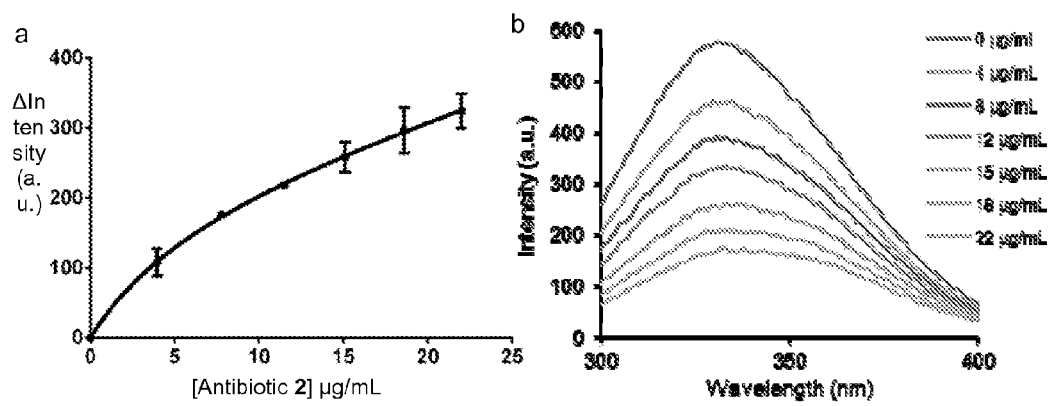

FIG. 11. Binding of quinazolinone 2 to PBP2a allosteric site. The intrinsic fluorescence of purified PBP2a (acylated at the active site by oxacillin prior to the experiment) was monitored during titration of antibiotic 2 into the mixture. (a) The change in the maximum fluorescence intensity was calculated as the difference compared to the intensity in the absence of compound. Any dilution effect was subtracted out using a buffer titration control. A $K_d$ of 6.8±2 μg/mL was obtained from the average of two individual experiments. A nonlinear regression was used to fit the data, with an $R^2$ of 0.9997. (b) Emission scans of PBP2a intrinsic fluorescence with excitation at 280 nm. Antibiotic 2 was titrated in to give the final concentrations shown and 3 scans (1 min cycles) were averaged for each titration.

Figure 12:
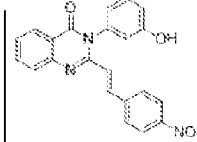
Figure 12:
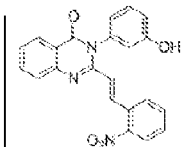
Figure 12:
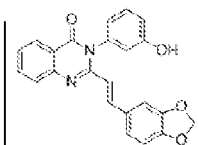
Figure 12:
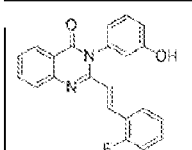
Figure 12:
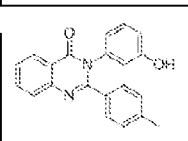
Figure 12:
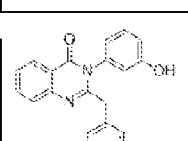
Figure 12:
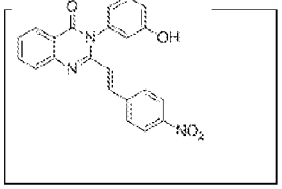
Figure 12:
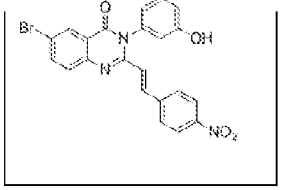
Figure 12:
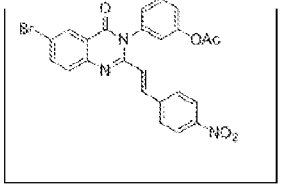
Figure 12:
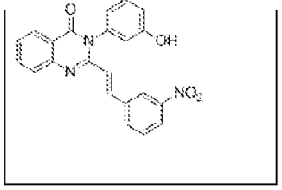
Figure 12:
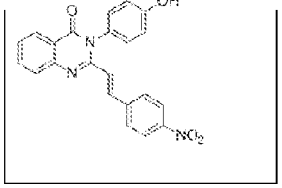
Figure 12:
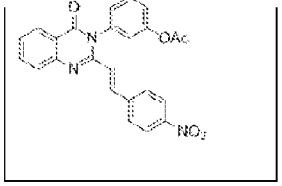
Figure 12:
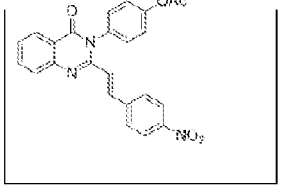
Figure 12:
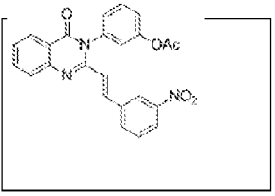
Figure 12:
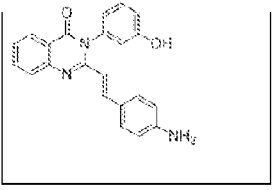
Figure 12:
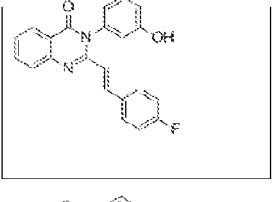
Figure 12:
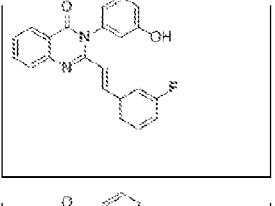
Figure 12:
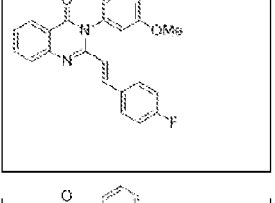
Figure 12:
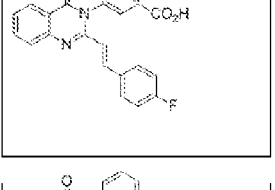
Figure 12:
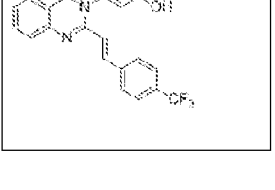
Figure 12:
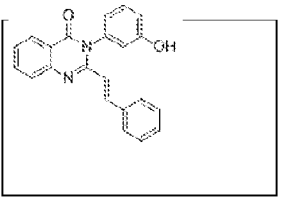
Figure 12:
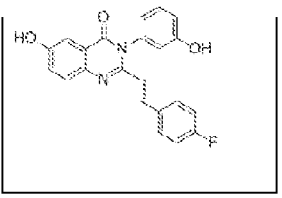
Figure 12:
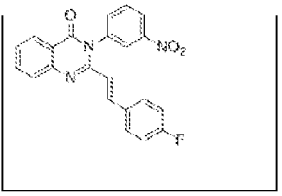
Figure 12:
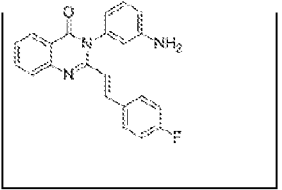
Figure 12:
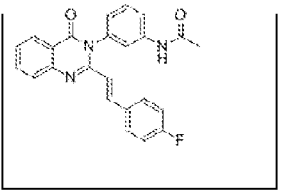
Figure 12:
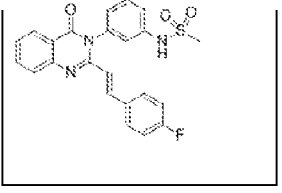
Figure 12:
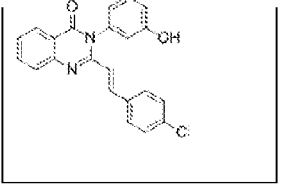
Figure 12:
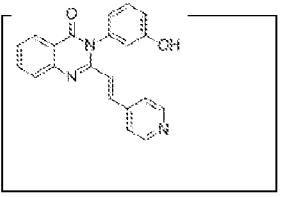
Figure 12:
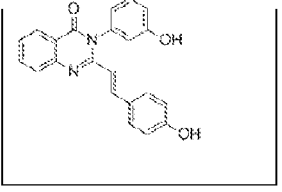
Figure 12:
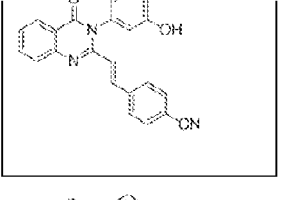
Figure 12:
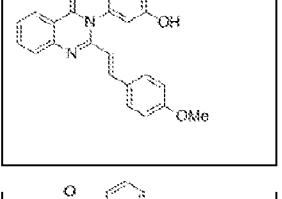
Figure 12:
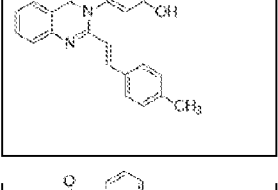
Figure 12:
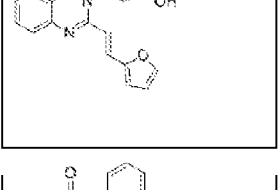
Figure 12:
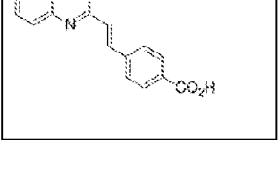
Figure 12:
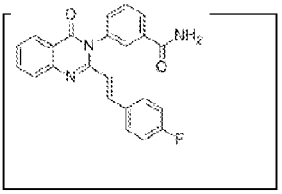
Figure 12:
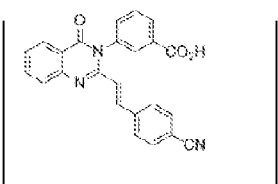
Figure 12:
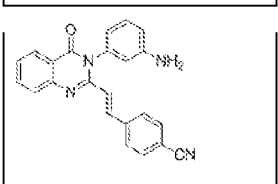
Figure 12:
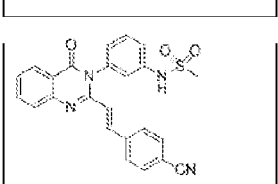
Figure 12:
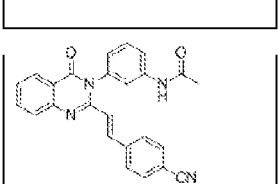
Figure 12:
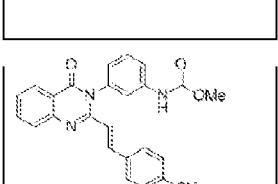
Figure 12:
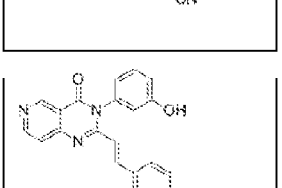
Figure 12:
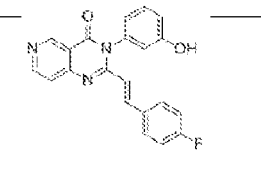
Figure 12:
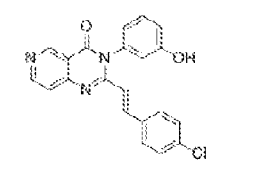
Figure 12:
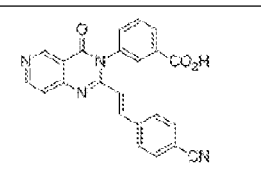
Figure 12:
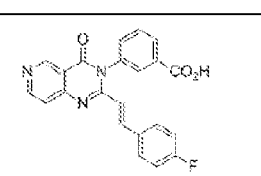
Figure 12:
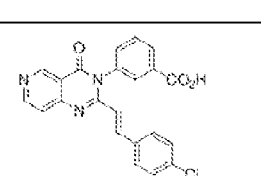
Figure 12:
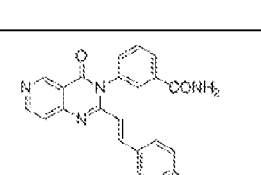
Figure 12:
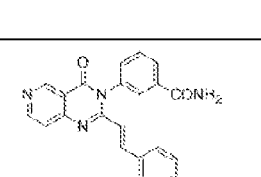
Figure 12:
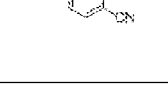
Figure 12:
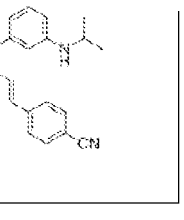
Figure 12:
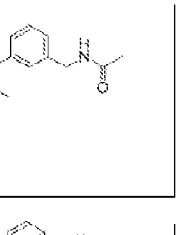
Figure 12:
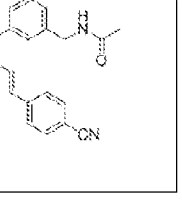
Figure 12:
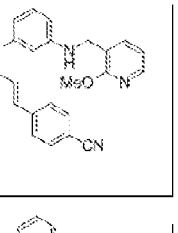
Figure 12:
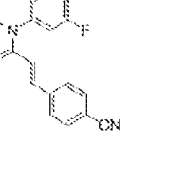
Figure 12:
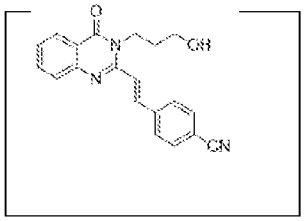
Figure 12:
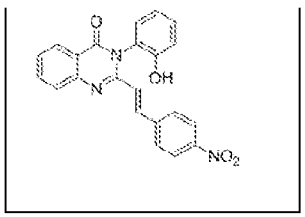
Figure 12:
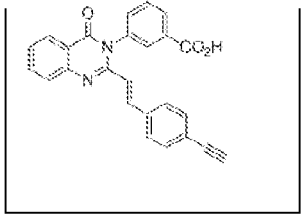

FIG. 12. Certain specific compounds of the invention and related data including Log P, MIC with respect to S. aureus ATCC 29213, and E. faecium NCTC 7171. *=MIC≤8; **=ΔMIC w/BSA≤8 fold. The compounds are active against gram positive bacteria only.

Figure 13:
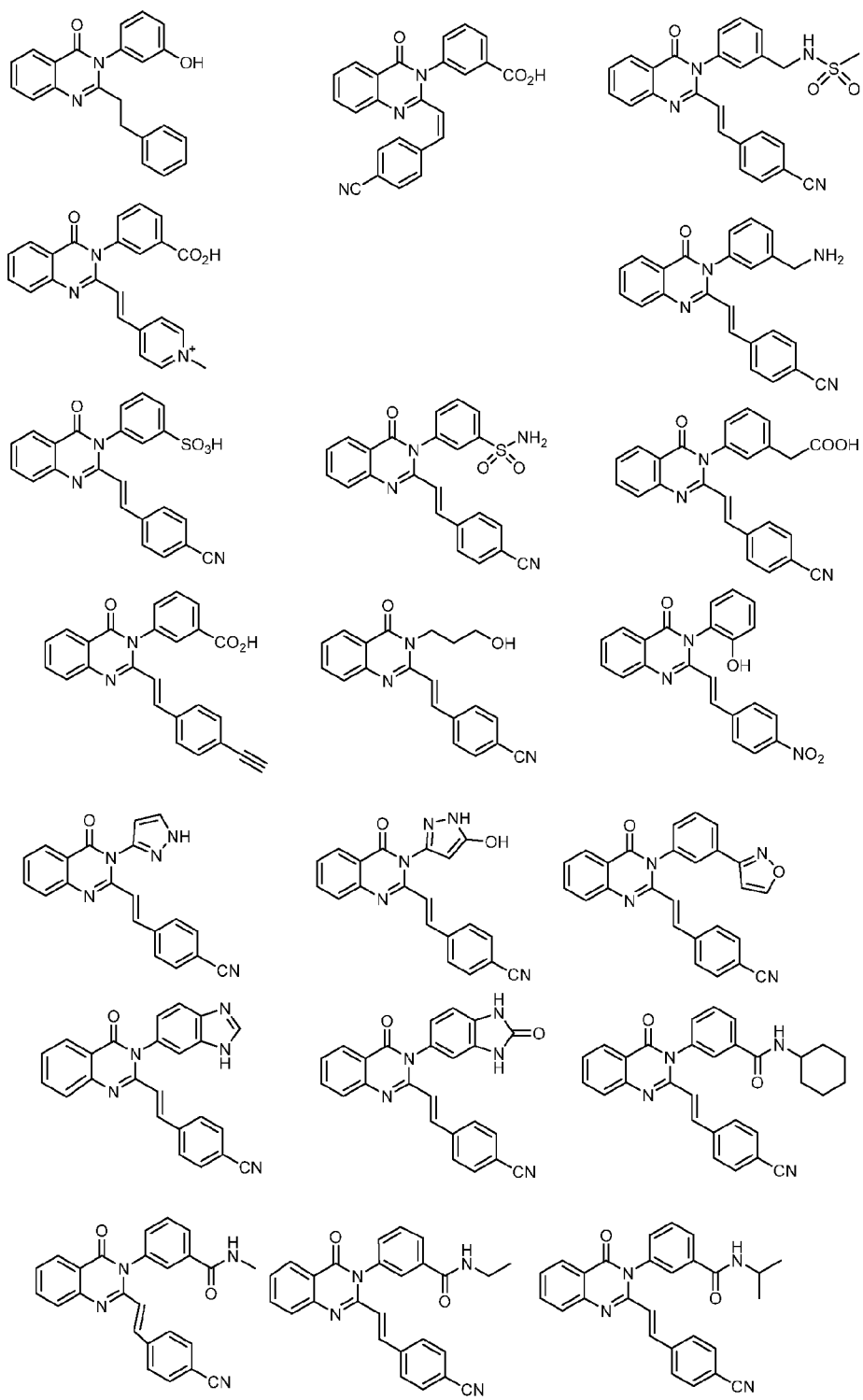
Figure 13:
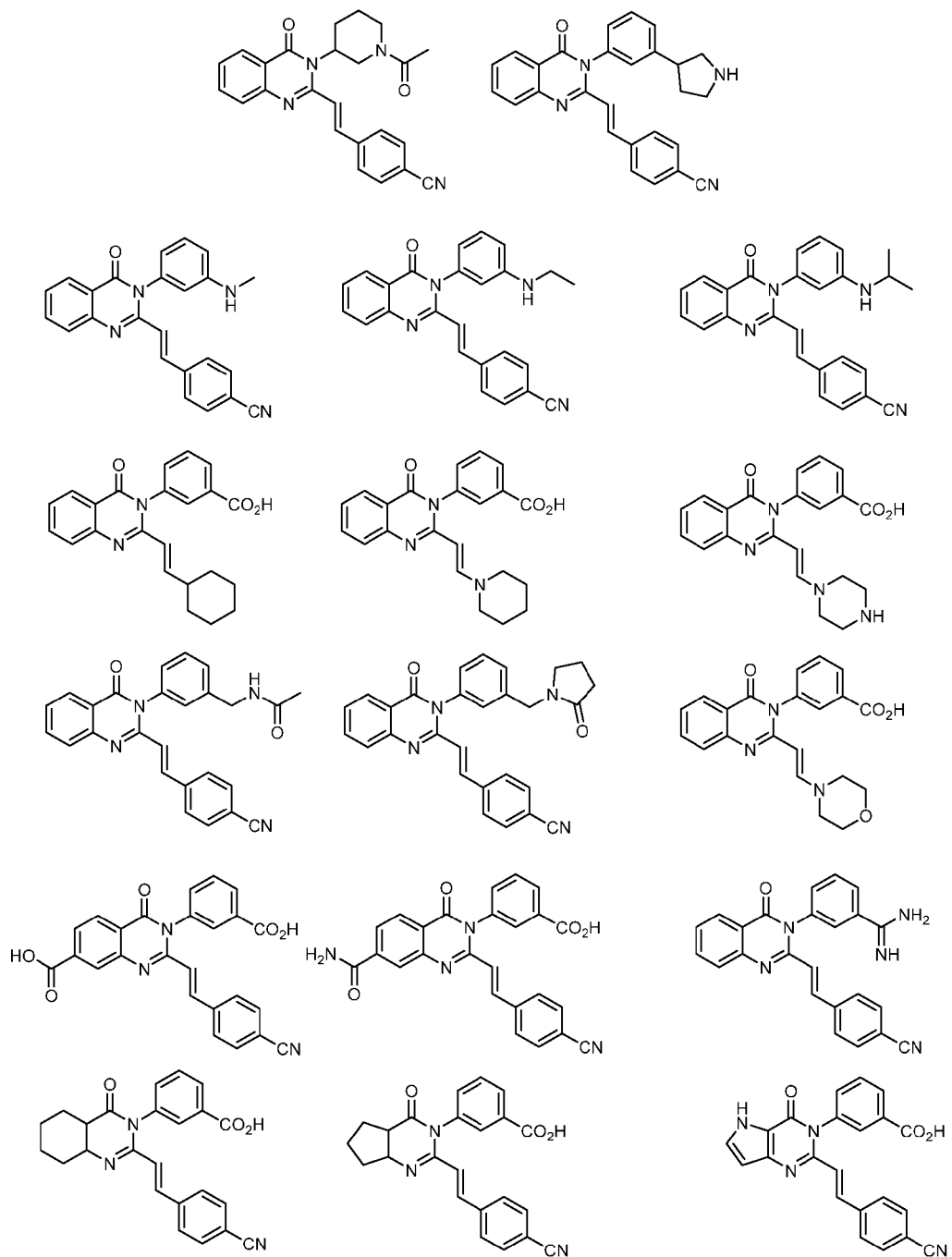

FIG. 13. Specific examples of quinazolinone compounds of the invention.

DETAILED DESCRIPTION

The need for new anti-MRSA agents is genuine, especially for antibiotics with oral bioavailability. Described herein are the first quinazolinone antibiotics with activities against Gram-positive bacteria, especially MRSA, inclusive of the hard-to-treat vancomycin- and linezolid-resistant variants. The quinazolinone antibiotics are orally bioavailable, they operate by an unprecedented mechanism of action, they exhibit antibacterial activity of their own both in vitro and in vivo, yet they also synergize with β-lactam antibiotics and can synergize with other classes of antibiotics.

Discovery of the Quinazolinone Class of Antibiotics. The X-ray structure of PBP-2a was used to screen by docking and scoring 1.2 million compounds from the ChemDiv drug-like subset of the ZINC database in silico using multiple scoring functions (Autodock, Glide, Gold, and ChemScore). The highest scoring 500 compounds were re-scored with Glide with greater stringency. Of these, 90 high ranking compounds were tested for antibacterial activity against the ESKAPE panel of bacteria (Enterobacter faecium, Staphylococcus aureus, Klebsiella pneumonia, Acetinobacter baumannii, Pseudomonas aeruginosa, and Enterobacter species, in addition to Escherichia coli); ESKAPE is the acronym for the first letters of the genus names. The members of the ESKAPE panel account for the majority of nosocomial infections. Quinazolinone 1 (Scheme 1) was discovered from this effort, with an MIC of 2 μg/mL against S. aureus ATCC29213 (methicillin-sensitive S. aureus, MSSA). However, the MIC of compound 1 increased to >128 μg/mL in the presence of serum albumin, indicating very high plasma protein binding, which could reduce the in vivo efficacy of an otherwise potent antibiotic.

Scheme 1. One Representative Quinazolinone Compound.

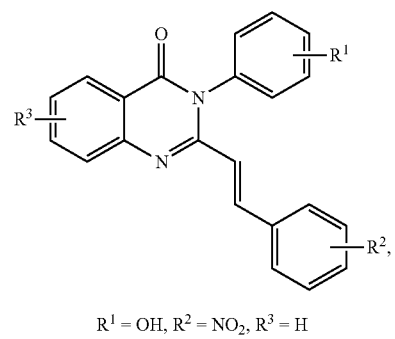

$R^1$ = OH, $R^2$ = $NO_2$, $R^3$ = H

We initiated lead optimization of this structural template to improve its in vitro potency, as well as to impart in vivo properties. We have synthesized 70 analogs of compound 1 and screened them for antibacterial activity. Highest in vitro activity was observed when the $R^1$ and $R^2$ groups were at the meta and para positions, respectively. We subsequently kept $R^1$ constant ($R^1$=OH), while varying $R^2$. The fluoro and nitrile analogs were found to be active, with the nitrile group exhibiting the highest potency. A few analogs with diverse $R^3$ groups were prepared, however in most cases this resulted in decrease in activity. Preliminary structure-activity relationship (SAR) study has yielded several potent anti-S. aureus agents with MICs of <2 μg/mL (Table 1). The quinazolinones have activity against Gram-positive bacteria, including MRSA (Table 2), but they are not active against the Gram-negative organisms in the ESKAPE panel.

TABLE 1

Summary of in vitro activity, pharmacokinetic properties, and in vivo efficacy ($R^1$ and $R^2$ refer to Scheme 1; $R^3$ = H).

| Cmpd | $R^1$ (m) | $R^2$ (p) | $MIC^a$ (w/ BSA) μg/mL | Mouse PK | Parameters[b] | In Vivo Efficacy[c] (survived/total mice) |
|---|---|---|---|---|---|---|
| 2 | —$CO_2H$ | —CN | 2 (8) | $AUC_{iv}$ = 1410<br>$AUC_{po}$ = 932<br>$V_d$ = 7.6<br>$t_{1/2, \beta\ iv}$ = 22 hr | CL = 7.1<br>F = 66% | 5/6 @ 10 mg/kg |
| 3 | —OH | —F | 0.25 (4) | AUC = 466<br>$V_d$ = 8.9 | CL = 10.7 | 1/6 @ 5 mg/kg |

TABLE 1-continued

Summary of in vitro activity, pharmacokinetic properties,
and in vivo efficacy ($R^1$ and $R^2$ refer to Scheme 1; $R^3$ = H).

| Cmpd | $R^1$ (m) | $R^2$ (p) | $MIC^a$ (w/ BSA) μg/mL | Mouse PK Parameters[b] | | In Vivo Efficacy[c] (survived/total mice) |
|---|---|---|---|---|---|---|
| 4 | —CO$_2$H | —F | 1 (8) | AUC = 2563 $V_d$ = 29.6 | CL = 7.8 | 3/6 @ 20 mg/kg |
| 5 | —NHCOCH$_3$ | —F | 1 (8) | AUC = 284 $V_d$ = 55.0 | CL = 88.2 | 2/6 @ 10 mg/kg |
| 6 | —NHSO$_2$CH$_3$ | —F | 0.125 (1) | AUC = 819 $V_d$ = 91.8 | CL = 28.0 | 0/6 @ 10 mg/kg |
| 7 | —OH | —CN | 0.03 (0.125) | AUC = 26.8 $V_d$ = 89.5 | CL = 186 | 1/6 @ 5 mg/kg |
| 8 | —NHCOCH$_3$— | —CN | 0.25 (2) | AUC = 1187 $V_d$ = 107 | CL = 131 | 1/6 @ 5 mg/kg |
| 9 | —NHSO$_2$CH$_3$ | —CN | 0.004 (0.03) | AUC = 31 $V_d$ = 98.5 | CL = 162 | 2/6 @ 5 mg/kg |

[a]*S. aureus* strain ATCC 29213 (MSSA);
[b]ICR female mice, compounds were dosed iv, compound 2 was also dosed orally (po), PK parameters after single dose iv administration, except for oral bioavailability, AUC = area under the concentration-time curve (μg · min/mL), CL = clearance (mL/min/kg), $V_d$ = volume of distribution (mL), F = oral bioavailability (%);
[c]Mouse peritonitis infection model, ICR female mice (n = 6) infected ip with MRSA ATCC 27660 at 5 × 10$^7$ cfu in 5% mucin. Leads were given iv at 30 min and 4.5 hr after infection, with vancomycin @ 5 mg/kg (6/6 mice survived) and vehicle (0/6 mice survived) as controls.

TABLE 2

Minimum-inhibitory concentrations (MIC, μg/mL)
of the quinazolinones against *S. aureus* strains.

| | 7 | 2 | 8 | 9 | vanco | linez-olid | oxacillin |
|---|---|---|---|---|---|---|---|
| *S. aureus* NRS70[a] | | 2 | | | 1 | 1 | 32 |
| *S. aureus* NRS100[b] | 0.25 | 16 | 1 | 0.5 | 2 | 2 | 512 |
| *S. aureus* NRS119[c] | 0.125 | 8 | 0.25 | 0.5 | 2 | 64 | 512 |
| *S. aureus* NRS120[c] | 0.125 | 8 | 0.25 | 0.25 | 2 | 64 | 512 |
| *S. aureus* NRS123[d] | | 2 | | | 1 | 2 | 32 |
| *S. aureus* VRS1[e] | 0.5 | 16 | 4 | 0.5 | >256 | 2 | 512 |
| *S. aureus* VRS2[f] | 0.06 | 2 | 0.125 | 0.125 | 64 | 1 | 256 |
| *S. epidermidis* ATCC 35547 | 0.125 | 1 | 0.06 | 0.125 | 64 | 1 | 128 |
| *S. haemolyticus* ATCC 29970 | 0.125 | 1 | 0.25 | 0.125 | 2 | 1 | 0.25 |

[a]Clinical MRSA strain isolated in Japan, mecA positive, resistant to erythromycin, clindamycin, oxacillin, and penicillin.
[b]MRSA strain isolated in Japan, mecA positive, resistant to oxacillin, penicillin, and tetracycline.
[c]Clinical MRSA strain, mecA positive, resistant to linezolid, ciprofloxacin, gentamicin, oxacillin, penicillin, and trimeth/sulfa.
[d]Community-acquired MRSA strain, mecA positive, resistant to methicillin, oxacillin, penicillin, and tetracycline.
[e]Clinical MRSA isolate from Michigan, mecA positive, vanA positive, resistant to linezolid, ciprofloxacin, gentamicin, oxacillin, penicillin, and trimeth/sulfa.
[f]Clinical MRSA isolate from Pennsylvania, mecA positive, vanA positive, resistant to vancomycin, ciprofloxacin, erythromycin, gentamicin, oxacillin, and penicillin.

We evaluated several compounds in in vivo mouse infection models, as well as in pharmacokinetic (PK) studies in mice (Table 1). The in vivo efficacy was determined using the rapid mouse peritonitis model of infection, in which the end point is death or survival in 48 hours. We initially dosed the compounds intravenously (iv) at a single dose level. If the compound has good in vivo efficacy after iv administration, we then evaluated efficacy at five dose levels. We also investigated in vivo efficacy after oral (po) administration. This study therefore not only tests efficacy in a mouse model of MRSA infection, but also requires the compounds to exhibit good PK properties in order to show efficacy in vivo.

We performed separate PK studies in mice to understand the in vivo efficacy results. We conducted first fast PK studies (n=2 mice per time point, 5 time points) dosing the compounds iv, followed by full PK studies for selected compounds (n=3 mice per time point, 10-12 time points per route of administration, iv and po). This allowed us to "weed" out compounds efficiently and spend more resources on the most worthy analogs. The most potent in vitro compound (9), with an MIC of 0.004 μg/mL, rescued only 2/6 mice due to its low systemic exposure (AUC=31 μg·min/mL) and very high clearance (CL=162 mL/min/kg). Whereas compound 2 exhibited a somewhat more modest in vitro MIC of 2 μg/mL, but had low clearance (CL=7.1 mL/min/kg) and higher systemic exposure (AUC=1410 μg·min/mL), and consequently had excellent in vivo efficacy, with a median effective dose (ED$_{50}$, the dose that results in survival of 50% of the animals) of 10 mg/kg after iv administration.

Figure 3:
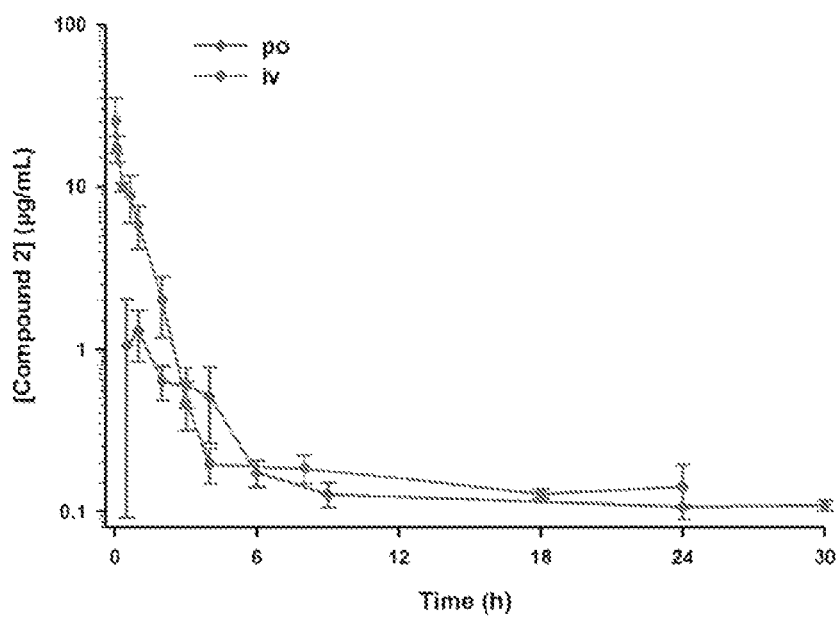
FIG. 3. Plasma concentrations of quinazolinone 2 in mice (n=3 per time point per route of administration) after single dose administration.

A full PK study with compound 2 was conducted after iv and po administration (FIG. 3). After a single 10 mg/kg iv dose of 2, plasma levels of 2 were sustained above MIC for 2 hours and declined slowly to 0.142±0.053 μg/mL at 24 hours. The compound had a volume of distribution of 0.3 L/kg, a long elimination half-life of 22 hours, and low clearance of 7.1 mL/min/kg, less than 10% of hepatic blood flow in mice. After a single 10 mg/kg po dose of 2, maximum concentrations of 1.29 μg/mL were achieved at 1 hour. The terminal half-life was long (58 h) and the absolute oral bioavailability was 66%.

In the XTT cell proliferation assay using HepG2 cells, compound 2 had an IC$_{50}$ of 63±1 μg/mL and showed no hemolysis (<1%) of red blood cells at 50 μg/mL, indicating that the compound was not toxic at concentrations in which antibacterial activity was documented. Furthermore, compound 2 was stable in mouse plasma (half-life of 141 h), and was metabolically stable (100% of 2 remaining after 1-h incubation) in rat and human S9 (liver fractions containing microsomes, including cytochrome P450 enzymes capable of phase I metabolism, and cytosol that contains transferases capable of phase II metabolism). Compound 2 (sodium salt) is water soluble, with a solubility of 8 mg/mL. Plasma protein binding of quinazolinone 2 was 98.0±0.04% in mice and 96.5±0.70% in humans.

Drugs bind to albumin, the most abundant protein in plasma. Forty three percent of the 1,500 frequently prescribed drugs on the market show protein binding greater than 90%, and 27% of anti-inflammatory drugs have protein binding above 99%. Moreover, many marketed antibiotics, including daptomycin, oxacillin, teicoplanin, rifampicin, and clindamycin have plasma protein binding of >91%.

Mechanism of Action of the Quinazolinones.

Figure 4:
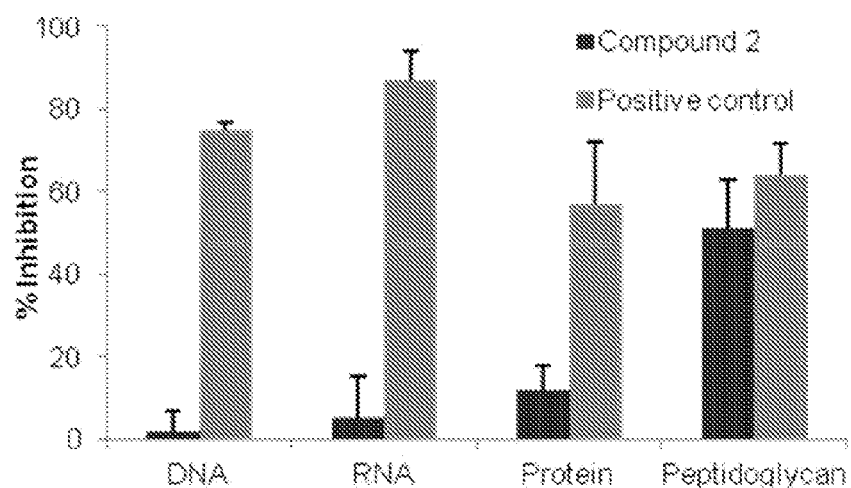
FIG. 4. Macromolecular Synthesis Assays. Compound 2 at 1 µg/mL, equivalent to ½ the MIC. Positive controls for DNA, RNA, protein, and peptidoglycan synthesis are ciprofloxacin (0.5 µg/mL), rifampicin (8 ng/mL), tetracycline (31 ng/mL), and fosfomycin (16 µg/mL), respectively.
Figure 5:
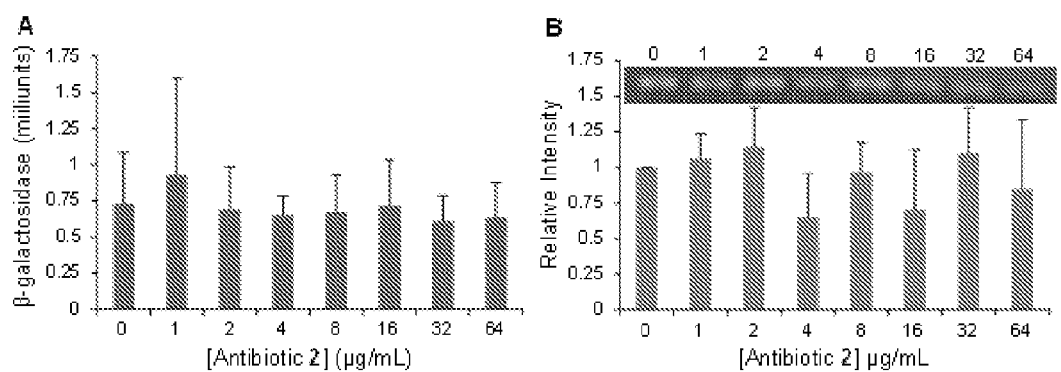
FIG. 5. Effect of quinazolinone 2 on in vitro transcription and translation. (A) A coupled transcription/translation assay using *E. coli* S30 extract system for circular DNA was performed in the presence of various amounts of 2. The amount of β-galactosidase was quantified in duplicate using the β-galactosidase enzyme assay system kit. A standard curve using known concentrations of β-galactosidase was prepared to convert absorbance readings to milliunits of β-galactosidase. No inhibition of in vitro translation was observed in the presence of up to 64 µg/mL antibiotic 2. (B) A transcription assay using a TranscriptAid T7 high yield transcription kit was performed in the presence of antibiotic 2. Samples were loaded in triplicate onto a denaturing 1% formaldehyde agarose gel and the band intensities analyzed and compared to the control (0 µg/mL antibiotic 2).

The mode of action of 2 was investigated by macromolecular synthesis assays in *S. aureus* in the logarithmic phase, which monitor incorporation of radiolabeled precursors [methyl-$^3$H]-thymidine, [5-$^3$H]-uridine, L-[4,5-$^3$H]-leucine, or D-[2,3-$^3$H]-alanine into DNA, RNA, protein, or cell wall (peptidoglycan), respectively. Inhibition of radiolabeled precursor incorporation by 2 at a concentration of half the MIC was compared with those of known inhibitors of each pathway (ciprofloxacin, rifampicin, tetracycline, and fosfomycin, respectively). As per our design paradigm, compound 2 showed notable inhibition of cell-wall biosynthesis in these assays (51±12% compared to 64±8% for fosfomycin) and did not significantly affect replication, transcription, or translation (FIG. 4). To further confirm these results, additional in vitro transcription and translation assays were performed using a T7 transcription kit and an *E. coli* S30 extract system coupled with a β-galactosidase assay system, respectively. Compound 2 did not show any inhibition of either transcription or translation using these in vitro assays (FIG. 5).

We next explored if it would inhibit purified recombinant PBP2a by a competition assay with Bocillin FL, a fluorescent penicillin reporter reagent. We purified PBP2a for this study using a previously described protocol from the laboratory of Prof. Mobashery (Fuda et al., *J. Biol. Chem.* 2004, 279, 40802-40806). This inhibition assay for PBPs has the limitation in that Bocillin FL is a covalent modifier of the active site of PBPs and the equilibrium is inexorably in favor of the irreversible acylation of the active-site serine by the reporter molecule. As such, the degree of inhibition by the non-covalent inhibitor (e.g., 2) will be underestimated.

Figure 6:
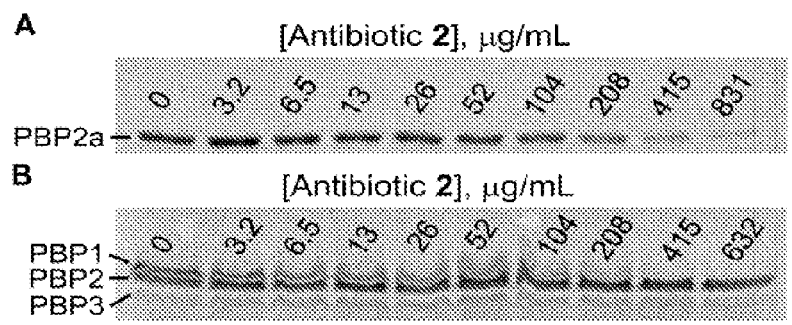
FIG. 6. Inhibition of Bocillin FL binding to *S. aureus* PBP2a and PBP1. (A) Fluorescence labeling of recombinant purified PBP2a (1 µM) by Bocillin FL (20 µM) in the presence of increasing amounts of antibiotic 2. (B) Fluorescence labeling of *S. aureus* membrane preparation (150 µg) by Bocillin FL (30 µM) in the presence of increasing amounts of antibiotic 2. Data were fit by nonlinear regression using the published equation,[1] with $R^2$ values of 0.95 and 0.87 for panels A and B, respectively.

Antibiotic 2 was able to inhibit Bocillin FL labeling of the active site of PBP2a in a competitive and dose-dependent manner, with an apparent IC$_{50}$ of 140±24 µg/mL, consistent with our design paradigm for binding of 2 at the active site (FIG. 6A). It is important to note that we have observed activity for quinazolinone 2 in strains of *S. aureus* that do not express PBP2a (Table 1), which indicates that the compound is likely to bind to other PBPs as well. This is akin to the case of β-lactam antibiotics, which bind to multiple PBPs due to high structural similarity at the active sites. To demonstrate the ability to bind to other PBPs, membrane preparations of *S. aureus* ATCC 29213 (an MSSA strain) were used to assess broader PBP inhibition by antibiotic 2. Inhibition of PBP1 was observed, with an apparent IC$_{50}$ of 78±23 µg/mL (FIG. 6B). Inhibition of PBP1 of *S. aureus* accounts for the antibacterial activity of meropenem, a carbapenem antibiotic. Because of the low-copy numbers of PBP2a in the membranes from MRSA, we could not demonstrate PBP2a inhibition in the membrane preparations directly. Inhibition of these PBPs by antibiotic 2 in living bacteria is expected to be more potent than what the Bocillin FL assay could evaluate, for the mechanistic reason that we described above.

As the quinazolinone class of antibiotics was discovered by in silico docking and scoring of compounds into the X-ray structure of PBP2a, we sought to determine the X-ray structure for the complex of quinazolinone 2 and PBP2a to validate the design paradigms. We purified soluble PBP2a using a variation of the methodology developed by the Mobashery lab and obtained crystals of PBP2a and of PBP2a-quinazolinone complexes using methods also developed recently in our labs (Otero et al., *Proc. Natl. Acad. Sci. USA* 2013, 110, 16808-16813).

Figure 7:
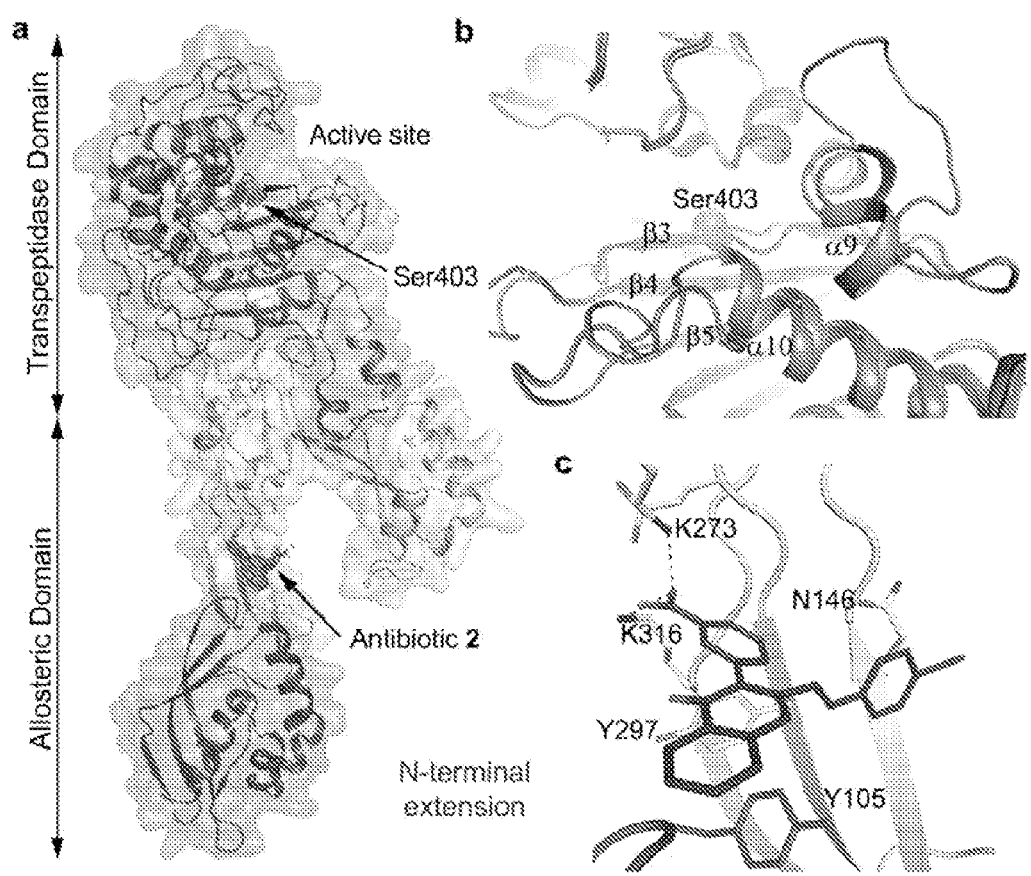
FIG. 7. Crystal structure of *S. aureus* PBP2a in complex with quinazolinone antibiotic 2. (A) Ribbon representation of PBP2a showing antibiotic 2 bound to the allosteric site, with electron density overlapped. The allosteric domain spans residues 27-326, where the N-terminal domain (residues 27-138) is shown at the bottom of (A) and the remaining allosteric domain is above it (central section of (A)). The transpeptidase domain (residues 327-668) is above the allosteric domain. Ligand density (mesh) is contoured at 1.0 σ from 2Fo-Fc feature-enhanced map refined electron density. (B) Ribbon superimposition at the active site of apo PBP2a (PDB ID: 1VQQ) and the complex. Major structural changes occur at loops α9-β3, β3-β4, and β5-α10. (C) Key interactions of antibiotic 2 at the allosteric site. Salt-bridge interactions with K273 and K316 are shown as dashed lines, the distances are 2.7 and 2.6 Å, respectively. Pi-stacking interactions are observed with Y105 and Y297.

The crystal structure of antibiotic 2 was solved and soaking experiments of PBP2a crystals with 2 resulted in a structure at 1.95-Å resolution for the complex. This structure revealed the density for antibiotic 2 bound to the allosteric site of PBP2a at 60-Å distance from the DD-transpeptidase active site (FIG. 7).

The critical binding of ligands such as the nascent cell-wall peptidoglycan at the allosteric site of PBP2a leads to the opening of the active site, enabling catalysis by PBP2a. The structure revealed alterations of spatial positions of certain residues (Lys406, Lys597, Ser598, Glu602, and Met641) within the active site of the complex, consistent with occupation by an antibiotic molecule, but density for it was not observed. However, we cannot rule out that these alternative active-site conformations could not have come about due to the allosteric conformational change. This observation, along with the earlier kinetic measurements exhibiting competition between Bocillin FL and 2, indicated that the antibiotic binds to the active site; however, the additional binding at the allosteric site was unanticipated.

Determination of the binding affinity at the allosteric site was performed using intrinsic fluorescence quenching of purified PBP2a, which had been modified covalently within the active site by the antibiotic oxacillin. Hence, compound 2 under these conditions would be expected to bind only to the allosteric site. A $K_d$ of 6.8±2 µg/mL was determined. Therefore, we have evidence for binding of antibiotic 2 to the allosteric site (X-ray) and to the active site (kinetic assays for competitive inhibition and X-ray altered conformations for the active-site residues) of PBP2a). Binding of antibiotic 2 at the allosteric site induces conformational changes at the active site (FIG. 7B). All of these movements serve to double the area and the volume of the active site.

PBP2a is a complex and large protein of about 75 kDa. The first X-ray structure for this protein showed the DD-transpeptidase active site of PBP2a sheltered. Based on the recent findings, this conformation is now referred to as the "closed" and inactive conformation. The "closed" conformation was confirmed by also solving the structure of the apo PBP2a. The closed conformation cannot accommodate entry of the cell-wall peptidoglycan, the PBP2a substrate. Neither can it allow penetration of β-lactam antibiotics into the active site, hence the broad resistance that MRSA shows to virtually all members of this class of antibiotics. The Mobashery lab showed a few years ago by kinetic experiments that the nascent peptidoglycan caused conformational changes in the protein that led to greater access to the active site (Fuda et al., *J. Am. Chem. Soc.* 2005, 127 (7), 2056-7).

Observation of this saturable process led to the proposal for the existence of allosteric activation of PBP2a, one that is triggered by the presence of the nascent peptidoglycan, the substrate for the enzyme. Interest in PBP2a recently led to the identification of the allosteric binding domain in PBP2a, which is remarkably 60 Å distant from the dd-transpeptidase active site. We have shown that indeed synthetic fragments of cell wall bind to the allosteric site and that they alter the conformation of the protein along one edge, which culminates in processes that lead to motion of two loops that open up the access to the active site (FIG. 7). The active site not only opens up, it also enlarges by roughly two-fold to be able to accommodate the two strands of peptidoglycan in its catalytic function (crosslinking of cell wall). This conformation of PBP2a is referred to as the "open" (catalytically competent) conformation.

When the X-ray structure of the complex of quinazolinone 2 bound to PBP2a was solved, we were surprised that we saw density for the quinazolinone at the allosteric site and not at the active site. The aforementioned kinetic experiments with Bocillin FL had clearly indicated that quinazolinone 2 bound to the active site (competitive mode of inhibition). Consistent with this expectation, the X-ray structure of the complex reveals reorganization of a few residues within the active site, indicative of potential interactions with the antibiotic, but density for 2 was not seen.

We presently have evidence for binding of the antibiotic to the allosteric site (X-ray) and to the active site (kinetic assays for competitive inhibition) of PBP2a. Interference with the function of PBP2a at both the allosteric and active sites works in concert in manifestation of the antibacterial activity. Allostery is absolutely critical for the function of PBP2a. Nonetheless, we have observed activity for the quinazolinone antibiotics in strains of S. aureus that do not express PBP2a, which indicates that the antibiotic is likely to bind to other PBPs in various organisms, akin to the case of β-lactam antibiotics. It is known that often more than one PBP is inhibited by β-lactams and the same is likely the case for the quinazolinone antibiotics described herein.

These compounds described herein are non-β-lactam, hence they do not suffer the shortcomings of β-lactam antibiotics in the face of widespread resistance to them. An additional interesting observation is the ability of quinazolinone 2 to stimulate allosteric opening of the active site, akin to the case of the nascent peptidoglycan in S. aureus, as indicated above. We have documented that synthetic surrogates of peptidoglycan can stimulate allostery, which leads to a major conformational change that propagates along the length of the protein to the active site, leading to opening up the active site for the crosslinking reaction. We see this very same process stimulated by the quinazolinone antibiotic by its binding to the allosteric site by the X-ray structure. Hence, notwithstanding the fact that the structure of the quinazolinone bears no resemblance to that of the peptidoglycan, they both bind to the allosteric site and we have X-ray evidence for both.

Synergy Between Quinazolinone and β-Lactam Antibiotics.

The binding of quinazolinone 2 to the allosteric site stimulates opening of the active site, as discussed above. The active site is normally closed, which is the basis for resistance to β-lactam antibiotics. Binding of a quinazolinone to the allosteric site can predispose PBP2a to inactivation by β-lactam antibiotics. Additionally, the quinazolinones described herein can synergize with β-lactams. This synergy can therefore resurrect presently obsolete β-lactam antibiotics in treatment of MRSA.

The checkerboard procedure (Eliopoulos et al., Antimicrobial Combinations. In *Antibiotics in Laboratory Medicine*, 4th Ed, 4 ed.; Lorian, V., Ed. Williams & Wilkins: Baltimore, Md., 1996) with oxacillin (a penicillin) or cefepime (a cephalosporin) and quinazolinones 2 or 9 was performed using the broth microdilution method in 96-well plates. The fractional-inhibitory concentrations (FIC) were calculated from $FIC=FIC_A+FIC_B$, where $FIC_A=[A]$ that inhibits growth in the combination divided by the MIC of A, and $FIC_B$ would be the same for antibiotic B. Synergism is defined as an FIC≤0.5, antagonism is an FIC>1, and additivity is an FIC=1.

Synergism was observed against MRSA strains NRS123 and NRS70 (Table 3), as evidenced by the concave isobolograms and FICs of 0.3 to 0.5. Addition of quinazolinone 2 or 9 (at ½ MIC) reduced the MIC of oxacillin by 16- to 32-fold and that of cefepime by 8- to 16-fold (Table 3). Oxacillin at ½ MIC was not effective alone, however in combination with quinazolinone resulted in >3 $log_{10}$ reduction in cfu/mL at 24 hours.

TABLE 3

Effect of combination of quinazolinones with β-lactam antibiotics on MIC against MRSA strains.

|  | MIC (µg/mL) NRS123[b] | MIC (µg/mL) NRS70[a] |
|---|---|---|
| quinazolinone 2 | 4 | 4 |
| quinazolinone 9 | 0.06 | 0.06 |
| oxacillin | 32 | 64 |
| oxacillin + 2[c] | 2 | 2 |
| oxacillin + 9[d] | 2 | 2 |
| cefepime | 32 | 64 |
| cefepime + 2[c] | 4 | 8 |
| cefepime + 9[d] | 4 | 4 |

[a]Clinical MRSA strain isolated in Japan, mecA positive, resistant to clindamycin, erythromycin, oxacillin, and penicillin G.
[b]A community-acquired MRSA strain isolated in the US, mecA positive, resistant to methicillin, oxacillin, penicillin G, and tetracycline.
[c]Combination of oxacillin or cefepime with 2 µg/mL quinazolinone 7.
[d]Combination of oxacillin or cefepime with 0.03 µg/mL quinazolinone 9.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation. For example, the R groups of the formulas described herein (e.g., $R^1$, $R^2$, $R^3$, $R^x$, $R^y$, and the like) can specifically exclude certain groups such as H, OH, halo, or specific halo groups including F, Cl, Br, or I, nitro, carboxy ($-CO_2H$), methoxy, methyl, trifluoromethyl, phenyl, nitrile, or any other group recited in the definitions of the R groups. The exclusion can be from one R group and not another. The exclusion can also be directed to a particular ortho, meta, or para position of a aryl or phenyl ring of one of the formulas. Accordingly, the formulas can exclude compounds that are known and/or that are not selected for a particular embodiment of the invention.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

With respect to in vitro assays and medical treatments, an "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The term "infection" refers to the invasion of the host by germs (e.g., bacteria) that reproduce and multiply, causing disease by local cell injury, release of poisons, or germ-antibody reaction in the cells. The infection can be in a mammal (e.g., a human).

With respect to chemical syntheses, an "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting, for example, with an effective amount of an antibacterial compound or composition described herein.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or optionally substituted, for example, with a substituent described below. The alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imino (C=NH), sulfinyl (SO) or sulfonyl (SO$_2$). Additionally, the alkyl can optionally be at least partially unsaturated, thereby providing an alkenyl.

The term "alkenyl" refers to a $C_2$-$C_{18}$ hydrocarbon containing normal, secondary, tertiary or cyclic carbon atoms with at least one site of unsaturation, i.e., a carbon-carbon, sp$^2$ double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$). The alkenyl can be a monovalent hydrocarbon radical, as described and exemplified above, or it can be a divalent hydrocarbon radical (i.e., alkenylene).

The alkenyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. Additionally, the alkenyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl (SO$_2$).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "acyl" group refers to a group containing a carbonyl moiety wherein the group is bonded via the carbonyl carbon atom. The carbonyl carbon atom is also bonded to another carbon atom, which can be part of an alkyl, aryl, arylalkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen atom, the group is a "formyl" group, an acyl group as the term is defined herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group. An acyloxy group is an acyl moiety connected to an oxygen, which group can form a substituent group.

The term "amino" refers to —NH$_2$. The amino group can be optionally substituted as defined herein for the term "substituted." The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The terms "amide" (or "amido") refer to C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H).

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The terms "aryloxy" and "arylalkoxy" refer to, respectively, an aryl group bonded to an oxygen atom and an arylalkyl group bonded to the oxygen atom at the alkyl moiety. Examples include but are not limited to phenoxy, naphthyloxy, and benzyloxy.

The term "aroyl" refers to an aryl-C(=O)— group.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or (C$_1$-C$_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The term "heterocycle" or "heterocyclyl" refers to a saturated or partially unsaturated ring system, containing at least one heteroatom selected from the group oxygen, nitrogen, and sulfur, and optionally substituted with alkyl, or C(=O)OR$^b$, wherein R$^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —OH, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$H, —S(=O)$_2$OH, —S(=O)$_2$R, —OS(=O)$_2$OR, —S(=O)$_2$NHR, —S(=O)R, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number will be determined as set forth above.

The term "pharmaceutically acceptable salts" refers to ionic compounds, wherein a parent non-ionic compound is modified by making acid or base salts thereof. Examples of pharmaceutically acceptable salts include, mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids. Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, behenic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can form pharmaceutically acceptable salts with various amino acids. For a review on pharmaceutically acceptable salts, see, e.g., Berge et al., *J. Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in *Remington: The Science and Practice of Pharmacy*, 21$^{st}$ edition, Lippincott, Williams & Wilkins, (2005).

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

The term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

The term "excipient" refers to an ingredient of the dosage form that is not medicinally active, but serves to dilute the API, assist in dispersion of the tablet in the patient's stomach, bind the tablet together, and serve other functions like stabilizing the API against decomposition.

METHODS OF THE INVENTION

Embodiments of the invention provide methods for killing bacteria or inhibiting the growth of bacteria using compounds described herein. As discussed above, various compounds in accordance with embodiments of the invention are designed to target penicillin-binding proteins. In other embodiments, compounds in accordance with embodiments of the invention may be designed to target other biological processes of bacteria.

In one embodiment, a method for inhibiting growth of bacteria is provided, comprising providing a source containing bacteria, and contacting the source with at least one compound described herein, such as a compound of a formula described herein, individually or in combination with other antibacterial compounds. In one embodiment, a bacterial infection in a human or an animal can be treated by administration of a compound described herein. In another embodiment, bacteria can be contacted with a compound described herein in vitro, for example, on an extracted sample or testing sample. In some embodiments, gram positive bacteria, and in particular, the PBPs on gram positive bacteria, can be effectively killed or inhibited. In certain embodiments, strains of *Enterococcus* and/or *Staphylococcus aureus* can be effectively killed or inhibited. In other embodiments, other bacterial strains may be targeted, such as but not limited to *M. tuberculosis, B. anthraces*, or others.

The quinazolinone compounds described herein can bind to the allosteric site of PBP2a and trigger opening of the active site. Beta-lactam antibiotics are not active against MRSA because they do not bind to the active site of PBP2a because the site is normally closed. Because the quinazolinone compounds described herein can bind to the allosteric site of PBP2a and trigger opening of the active site, they can act synergistically with other antibacterial agents, including beta-lactams, the synergy with which has been demonstrated with the quinazolinone compounds described herein. Thus, the quinazolinones open a new strategy for resurrection of now defunct beta-lactam antibiotics for the effective treatment of bacterial infections.

Accordingly, the invention provides compositions that include a compound of a formula described herein, or a specific compound described herein, in combination with a second antibacterial agent. One class of antibacterial agents that can act synergistically when combined with a compound described herein for the treatment of a bacterial infection is the beta-lactam antibiotics. One specific antibacterial agent that can be combined with a compound described herein is ceftaroline. Other classes of antibacterial agents that can act synergistically when combined with a compound described herein for the treatment of a bacterial infection include aminoglycosides, tetracyclines, sulfonamides, fluoroquinolones, macrolides, polymyxins, glycylcyclines, and lincosamides.

Other antibacterial agent that can be used in combination with a compound described herein include, but are not limited to, amoxicillin, ampicillin, azlocillin, mezlocillin, apalcillin, hetacillin, bacampicillin, carbenicillin, sulbenicillin, ticarcillin, azlocillin, mecillinam, pivmecillinam, methicillin, ciclacillin, talampicillin, aspoxicillin, oxacillin, cloxacillin, dicloxacillin, flucloxacillin, nafcillin, pivampicillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefinenoxime, cefinetazole, cephaloglycin, cefonicid, cefodizime, cefpirome, ceftazidime, ceftriaxone, cefpiramide, cefbuperazone, cefozopran, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil cefditoren pivoxil, cefuroxime, cefuroxime axetil, daptomycin, loracarbacef, latamoxef and pharmaceutically acceptable salts, solvates or prodrugs thereof.

Additional antibacterial agent that can be used in combination with a compound described herein include, but are not limited to, cephalosporins, such as cefepime or a pharmaceutically acceptable salt, solvate or prodrug thereof; monobactams such as aztreonam or carumonam or a pharmaceutically acceptable salt, solvate or prodrug thereof; glycylcyclines such as tigecycline or a pharmaceutically acceptable salt, solvate or prodrug thereof; aminoglycosides, including, but not limited to, amikacin, gentamicin, kanamycin, neomycin, netilmicin, paromomycin, streptomycin, tobramycin and pharmaceutically acceptable salts, solvates or prodrugs thereof; carbapenems, including, but not limited to, imipenem, biapenem, meropenem, ertapenem, faropenem, doripenem, panipenem, PZ-601 and pharmaceutically acceptable salts, solvates or prodrugs thereof; macrolide, including, but not limited to, erythromycin, azithromycin, dirithromycin, telithromycin, clarithromycin and pharmaceutically acceptable salts, solvates or prodrugs thereof; fluoroquinolones, including, but not limited to, levofloxacin, ciprofloxacin, ofloxacin, gatifloxacin, norfloxacin, moxifloxacin, trovafloxacin and pharmaceutically acceptable salts, solvates or prodrugs thereof; acylaminopenicillins, such as piperacillin or a pharmaceutically acceptable salt, solvate or prodrug thereof; tazobactam or a pharmaceutically acceptable salt, solvate or prodrug thereof; daptomycin or a pharmaceutically acceptable salt, solvate or prodrug thereof.

The two antibacterial agents can be administered together, or they can be administered sequentially. In various embodiments, a compound described herein and a second antibacterial agents, for example, one recited above, can be administered in a combined dose of about 1 mg to 20 g/day in single or multiple administrations. In other embodiments, the combined dose may range from about 10 mg to 10 g/day. In still other embodiments, the combined dose may range from about 20 mg to 5 g/day. In certain embodiments, the combined dose may range from about 30 mg to 2 g/day. In certain specific embodiments, the combined daily dose may be about 20 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2750 mg, 2800 mg, 2850 mg, 2900 mg, 2950 mg, 3000 mg, 3.5 g, 4 g, 4.5 g, 5 g, 5.5 g, 6 g, 6.5 g, 7 g, 7.5 g, 8 g, 8.5 g, 9 g, 9.5 g or 10 g.

In certain embodiments, a compound described herein or a pharmaceutically acceptable salt, solvate or prodrug thereof can be administered in a daily dose ranging from about 0.5 mg/kg to about 400 mg/kg, preferably from about 2 mg to 40 mg/kg, of body weight of a human or an animal infected with pathogenic bacteria. In still other embodiments, the daily dose may range from about 5 to 30 mg/kg of body weight. In some embodiments, the daily dose may be about 20 mg/kg of body weight. In some embodiments, the daily dose may be administered in a singular dose, for example, every 24 hours. In other embodiments, the daily dose may be administered in two to six divided doses, for example, every 4 hours, 6 hours, 8 hours or 12 hours.

In some embodiments, a compound described herein or a pharmaceutically acceptable salt, solvate or prodrug thereof can be administered in doses ranging from about 1 mg to about 3000 mg per day in single or multiple administrations. In some embodiments, a compound described herein or a pharmaceutically acceptable salt, solvate or prodrug thereof may be administered in single or multiple doses of about 10 mg, 20 mg, 30 mg, 40 mg, 50 mg, 100 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg and 1800 mg per day. For example, the daily dose of a compound described herein or a pharmaceutically acceptable salt, solvate or prodrug thereof can be about 400 mg, about 600 mg, about 800 mg or about 1200 mg. The duration of treatment can be, for example, between five to seven days, five to ten days, five to fourteen days, or five to 21 days.

In some embodiments, the bacterial infection may be due to Gram-positive bacteria, including, but not limited to, methicillin resistant *Staphylococcus aureus* (MRSA), community-acquired methicillin resistant *Staphylococcus aureus* (CAMRSA), vancomycin-intermediate-susceptible *Staphylococcus aureus* (VISA), methicillin-resistant coagulase-negative staphylococci (MR-CoNS), vancomycin-intermediate-susceptible coagulase-negative staphylococci (VI-CoNS), methicillin susceptible *Staphylococcus aureus* (MSSA), *Streptococcus pneumoniae* (including penicillin-resistant strains [PRSP]) and multi-drug resistant strains [MDRSP]), *Streptococcus agalactiae, Streptococcus pyogenes* and *Enterococcus faecalis*. In particular embodiments, the bacterial infection may include, but is not limited to, complicated skin and skin structure infections (cSSSI); community acquired pneumonia (CAP); complicated intra-abdominal infections, such as, complicated appendicitis, peritonitis, complicated cholecystitis and complicated diverticulitis; uncomplicated and complicated urinary tract infections, such as, pyelonephritis; and respiratory and other nosocomial infections.

General Synthetic Methods

Preparation of the compounds described herein can be prepared according to the methods in the Examples below, or may be prepared according to known techniques in the art of organic synthesis. Many alkynes, allenes, and linking groups are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Additional useful reactions well known to those of skill in the art are referenced in March's *Advanced Organic Chemistry Reactions, Mechanisms, and Structure*, 5th Ed. by Michael B. Smith and Jerry March, John Wiley & Sons, Publishers; and Wuts et al. (1999), *Protective Groups in Organic Synthesis*, 3rd Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The quinazolinone compounds described herein can be prepared using standard synthetic techniques known to those of skill in the art. Examples of such techniques are described by Khajavi et al. (*J. Chem. Res.* (S), 1997, 286-287) and Mosley et al. (*J. Med. Chem.* 2010, 53, 5476-5490). A general preparatory scheme for preparing the compounds described herein, for example, compounds of Formula A) is as follows.

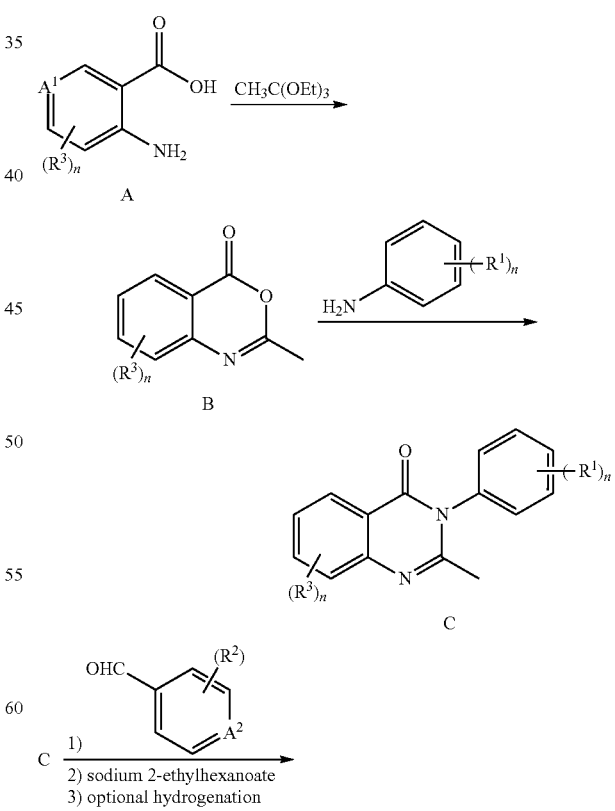

-continued

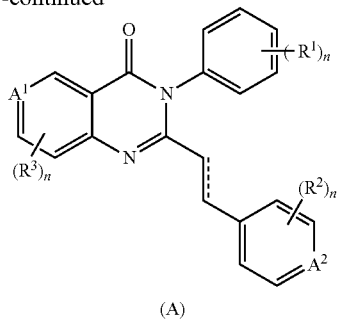

(A)

wherein each of the variables are as defined for one or more of the formulas described herein, such as Formula (A). Starting materials are readily available from chemical suppliers such as Sigma-Aldrich, Aurora Fine Chemicals, Acorn Pharmatech, Attomax Chemicals, Fluka, and Acros Organics. Other starting materials can be readily prepared in one to a few steps using standard synthetic transformations familiar to those of skill in the art.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating bacterial infections in a mammal, which involve administering to a mammal having a bacterial infection an effective antibacterial amount of a compound or composition described herein. A mammal includes a primate, human, rodent, canine, feline, bovine, ovine, equine, swine, caprine, bovine and the like.

The ability of a compound of the invention to treat a bacterial infection may be determined by using assays well known to the art. For example, the design of treatment protocols, toxicity evaluation, data analysis, quantification of bacteria cell kill, and the biological significance of the use of in vitro screens are known. In addition, ability of a compound to treat a bacterial infection may be determined using the tests as described herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Compound Preparation

Chemistry.

Organic reagents and solvents were purchased from Sigma-Aldrich. $^1$H and $^{13}$C NMR spectra were recorded on a Varian INOVA-500. High-resolution mass spectra were obtained using a Bruker micrOTOF/Q2 mass spectrometer.

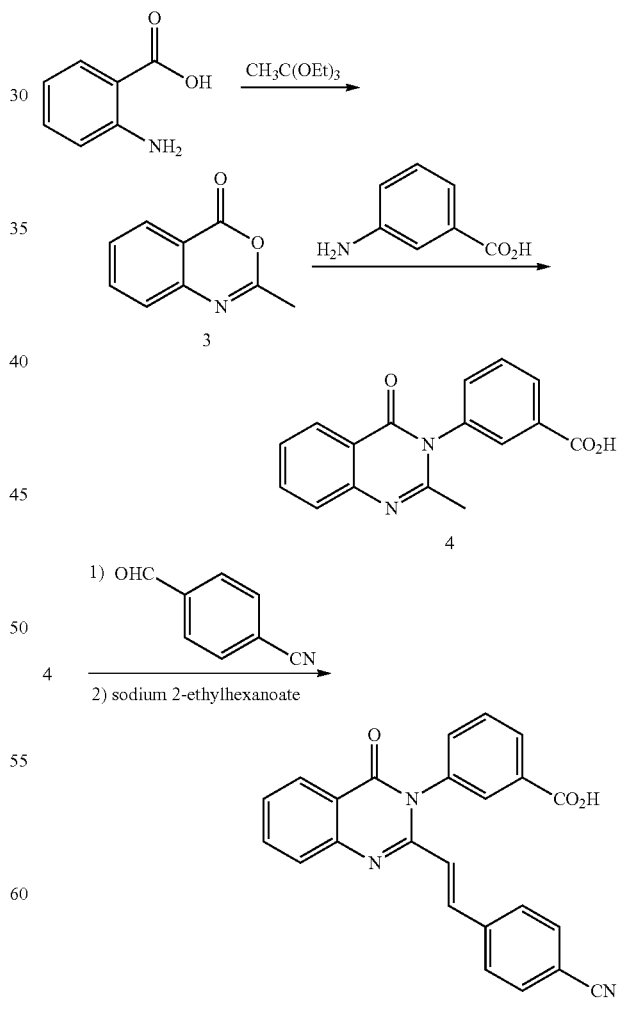

2-Methyl-4H-benzo[d][1,3]oxazin-4-one (3)

Anthranilic acid (20 g, 146 mmol) was dissolved in triethyl orthoacetate (45 mL, 245 mmol) and refluxed for 2 h. The reaction mixture was cooled on ice for 4 h to crystallize the intermediate. The resulting crystals were filtered and washed with hexanes to give 3 (17 g, 72% yield). $^1$H NMR (500 MHz, CDCl$_3$) δ 2.47 (s, 3H), 7.50 (t, J=7.38 Hz, 1H), 7.54 (d, J=7.98 Hz, 1H), 7.80 (t, J=7.18 Hz, 1H), 8.18 (d, J=7.78 Hz, 1H). $^{13}$C NMR (126 MHz, CDCl$_3$) δ 21.59, 116.84, 126.59, 128.42, 128.66, 136.77, 146.61, 159.89, 160.45. HRMS (m/z): [M+H]$^+$, calcd for C$_9$H$_8$NO$_2$, 162.0550; found, 162.0555.

2-Methyl-3-(3-carboxyphenyl)-quinazolin-4(3H)-one (4)

Compound 3 (2 g, 12.4 mmol) and 3-aminophenol (1.7 g, 12.4 mmol) were suspended in glacial acetic acid (8 mL, 140 mmol), and dissolved upon heating. The reaction was refluxed for 5 h, at which point 5 mL water was added to the cooled reaction mixture. The resulting precipitate was filtered and washed with water, followed by cold ethanol and hexane to give 4 (3.19 g, 92% yield). $^1$H (500 MHz, DMSO-d$_6$) δ 2.87 (s, 3H), 7.52 (t, J=7.38 Hz, 1H), 7.66-7.73 (m, 3H), 7.84 (t, J=7.38 Hz, 1H), 8.01 (s, 1H), 8.09 (t, J=7.58 Hz, 2H). $^{13}$C NMR (126 MHz, DMSO-d$_6$) δ 24.13, 120.48, 126.32, 126.47, 126.72, 129.52, 129.83, 130.01, 132.40, 133.07, 134.67, 138.18, 147.37, 154.13, 161.44, 166.58. HRMS (m/z): [M+H]$^+$, calcd for C$_{16}$H$_{13}$N$_2$O$_3$, 281.0921; found, 281.0917.

Sodium (E)-3-(3-carboxyphenyl)-2-(4-cyanostyryl)quinazolin-4(3H)-one (2)

Compound 4 (1.0 g, 3.6 mmol) and 4-formylbenzonitrile (0.56 g, 4.3 mmol) were suspended in glacial acetic acid (5 mL, 87 mmol), a suspension that dissolved upon heating. The reaction was refluxed for 18 h and 5 mL water was added to the cooled reaction mixture. The resulting precipitate was filtered and washed with water, followed by cold ethanol and hexanes to afford the carboxylic acid (0.77 g, 75% yield). HRMS (m/z): [M+H]$^+$, calcd for C$_{24}$H$_{16}$N$_3$O$_3$, 394.1186; found 394.1214. The carboxylic acid (0.45 g, 1.1 mmol) was dissolved in hot ethanol, to which sodium 2-ethylhexanoate (0.28 g, 1.7 mmol) was added. The reaction mixture was stirred on ice for 2 h. The precipitate was filtered and washed with cold ethanol. The product was obtained by dissolving the precipitate in about 5 mL of water and subsequent lyophilization of the solution to give 2 as the sodium salt (0.4 g, 85% yield). $^1$H NMR (500 MHz, DMSO-d$_6$) δ 6.47 (d, J=15.55 Hz, 1H), 7.59 (m, 3H), 7.74 (d, J=5.38 Hz, 2H), 7.79 (m, 3H), 7.91 (m, 2H), 8.05 (s, 1H), 8.14 (d, J=7.78 Hz, 2H). $^{13}$C NMR (126 MHz, DMSO-d$_6$) δ 111.56, 118.61, 120.76, 123.42, 126.50, 127.01, 127.35, 128.26, 129.99, 130.06, 130.12, 132.33, 132.83, 133.46, 134.89, 136.95, 137.03, 139.25, 147.21, 150.74, 161.25, 166.52. HRMS (m/z): [M+H]$^+$, calcd for C$_{24}$H$_{15}$N$_3$NaO$_3$, 416.1006; found, 416.0987.

Example 2. Discovery of Quinazolinones as an Antibiotic Class Active Against Methicillin-Resistant *Staphylococcus aureus*

Figure 1:
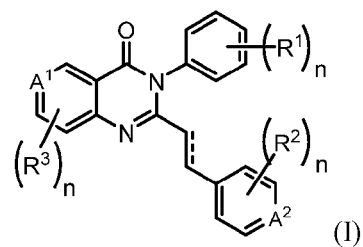
FIG. 1. A generic formula of compounds of the invention.
Figure 2:
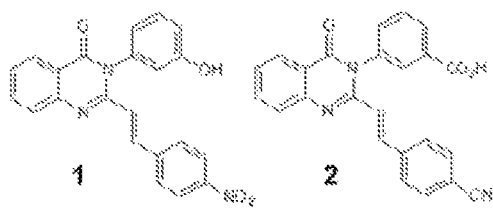
FIG. 2. Two specific quinazolinones of the invention.

We used the X-ray structure of PBP2a to computationally screen 1.2 million drug-like compounds from the ZINC database using cross-docking with multiple scoring functions. Starting with high-throughput virtual screening, the filtering was stepwise with increasing stringency, such that at each stage the best scoring compounds were fed into the next stage. The final docking and scoring step involved Glide refinement of docking poses with the extra precision mode, where the top 2,500 poses were clustered according to structural similarity. Of these, 118 high ranking samples were tested for antibacterial activity against *Escherichia coli* and the ESKAPE panel of bacteria, which account for the majority of nosocomial infections. Antibiotic 1 (FIG. 2) was discovered in this effort, with a minimal-inhibitory concentration (MIC) of 2 μg/mL against *S. aureus* ATCC29213 (a methicillin-sensitive *S. aureus*, MSSA) of the ESKAPE panel; however the MIC increased to >128 μg/mL in the presence of bovine serum albumin (BSA), indicating high plasma protein binding. The compound did not have activity against Gram-negative bacteria of our panel.

We initiated lead optimization of this structural template to maintain its in vitro potency, while imparting in vivo properties. We synthesized 70 analogs of compound 1 (FIG. 12) and screened them for in vitro antibacterial activity, metabolic stability, in vitro toxicity, efficacy in an in vivo mouse MRSA infection model, plasma protein binding, and pharmacokinetics (PK). Antibiotic 2 (FIG. 2) emerged from these studies with the desired attributes, including efficacy in a mouse infection model.

Antibiotic 2 was synthesized using a variation of a previously reported method for construction of the quinazolinone core (Mosley, C A et al. *J. Med. Chem.* 53, 5476-5490 (2010); Khajavi, M S, Montazari, N & Hosseini, S S S. *J. Chem. Research.* (S), 286-287 (1997)). Antibiotic 2 showed activity against MRSA strains similar to those of linezolid and vancomycin. Furthermore, activity was documented against vancomycin- and linezolid-resistant MRSA strains (Table 2.1).

TABLE 2.1

In vitro AB activity of quinazolinone 2 against a panel of Staphylococcal strains.

|  | 2 | vancomycin | linezolid | oxacillin |
|---|---|---|---|---|
| *S. aureus* ATCC 29213[a] | 2 | 1 | 4 | 0.25 |
| *S. aureus* NRS128[b] | 4 | 1 | 1 | 0.5 |
| *S. aureus* NRS70[c] | 2 | 1 | 1 | 32 |
| *S. aureus* NRS123[d] | 2 | 1 | 2 | 32 |
| *S. aureus* NRS100[e] | 16 | 2 | 2 | 512 |
| *S. aureus* NRS119[f] | 8 | 2 | 32 | 512 |
| *S. aureus* NRS120[f] | 8 | 2 | 32 | 512 |
| *S. aureus* VRS1[g] | 16 | 512 | 2 | 512 |
| *S. aureus* VRS2[h] | 2 | 64 | 2 | 256 |
| *S. epidermidis* ATCC 35547 | 1 | 16 | 1 | 128 |
| *S. haemolyticus* ATCC 29970 | 1 | 2 | 2 | 0.25 |

[a]Quality control MSSA strain;
[b]MSSA strain, mecA negative, resistant to erythromycin, clindamycin, and penicillin;
[c]Clinical MRSA strain isolated in Japan, mecA positive, resistant to erythromycin, clindamycin, oxacillin, and penicillin;
[d]Community-acquired MRSA strain, mecA positive, resistant to methicillin, oxacillin, penicillin, and tetracycline;
[e]MRSA strain, mecA positive, resistant to oxacillin, penicillin, and tetracycline;
[f]Clinical MRSA strain, mecA positive, resistant to linezolid, ciprofloxacin, gentamicin, oxacillin, penicillin, and trimeth/sulfa;
[g]Clinical MRSA isolate from Michigan, mecA positive, vanA positive, resistant to vancomycin, ciprofloxacin, clindamycin, erythromycin, gentamicin, oxacillin, and penicillin;
[h]Clinical MRSA isolate from Pennsylvania, mecA positive, vanA positive, resistant to vancomycin, ciprofloxacin, clindamycin, erythromycin, gentamicin, oxacillin, and penicillin.

The MIC values increased 4-fold in the presence of BSA, indicating that plasma protein binding was not very high. In the XTT cell proliferation assay using HepG2 cells, antibiotic 2 had an IC$_{50}$ of 63±1 μg/mL and showed no hemolysis (<1%) of red blood cells at 50 μg/mL, indicating that the compound was not toxic at concentrations in which antibacterial activity was documented. Furthermore, antibiotic 2 was stable in mouse plasma (half-life of 141 h), and was metabolically stable (100% of 2 remaining after 1-h incubation) in rat and human S9, liver fractions containing microsomes (including cytochrome P450 enzymes capable of phase I metabolism) and cytosol (containing transferases capable of phase II metabolism). Antibiotic 2 (sodium salt) is also water soluble, with a solubility of 8 mg/mL.

Quinazolinone 2 demonstrated excellent in vivo efficacy in the mouse peritonitis model of MRSA infection (Gross, M et al. *Antimicrob. Agents Chemother.* 47, 3448-57 (2003)), with a median effective dose ($ED_{50}$, the dose that results in survival of 50% of the animals) of 10 mg/kg after intravenous (iv) administration. After a single 10 mg/kg iv dose of 2, plasma levels of 2 were sustained above MIC for 2 hours and declined slowly to 0.142±0.053 µg/mL at 24 hours (further discussed below; see FIG. 3). The compound had a volume of distribution of 0.3 L/kg (Table 2.2), a long elimination half-life of 22.3 hours, and low clearance of 7.07 mL/min/kg, less than 10% of hepatic blood flow in mice. After a single 10 mg/kg oral (po) dose of 2, maximum concentrations of 1.29 µg/mL were achieved at 1 hour. The terminal half-life was long (58.2 h) and the absolute oral bioavailability was 66%.

TABLE 2.2

Pharmacokinetic parameters of quinazolinone 2 in mice after single iv or po dose administration.

| Parameter | po | iv |
| --- | --- | --- |
| Dose (mg/kg) | 10 | 10 |
| $AUC_{0\text{-}last}$ (µg · min/mL) | 393 | 1180 |
| $AUC_{0\text{-}\infty}$ (µg · min/mL) | 932 | 1410 |
| Vd (mL/kg) | — | 303 |
| CL (mL/min/kg) | — | 7.07 |
| $C_0$ (µg/mL) | — | 33.0 |
| $t_{1/2 absorption}$ (h) | 0.411 | — |
| $t_{1/2 distribution}$ (h) | 2.06 | 0.242 |
| $t_{1/2 elimination}$ (h) | 58.2 | 22.3 |
| $C_{max}$ (µg/mL) | 1.29 | — |
| $T_{max}$ (min) | 60.0 | — |
| F (%) | 65.9 | — |

$AUC_{0\text{-}last}$ = area under the concentration-time curve from time zero to the last time point
$AUC_{0\text{-}\infty}$ = area under the concentration-time curve from time zero to infinity
Vd = volume of distribution, calculated by Dose/$C_0$
CL = clearance, calculated by Dose/$AUC_{0\text{-}\infty}$
$C_0$ = concentration at time zero
$C_{max}$ = maximum concentration
$T_{max}$ = time at maximum concentration
F = absolute oral bioavailability, calculated by $AUC_{0\text{-}last\ po}/AUG_{0\text{-}\infty\ iv}$ The mode of action of 2 was investigated by macromolecular synthesis assays in *S. aureus* in the logarithmic phase (Miller, A A et al. *Antimicrob. Agents Chemother.* 52, 2806-12 (2008)), which monitor incorporation of radiolabeled precursors [methyl-$^3$H]-thymidine, [5-$^3$H]-uridine, L-[4,5-$^3$H]-leucine, or D-[2,3-$^3$H]-alanine into DNA, RNA, protein, or cell wall (peptidoglycan), respectively. Inhibition of radiolabeled precursor incorporation by antibiotic 2 at a concentration of 0.5 MIC was compared with those of known inhibitors of each pathway (ciprofloxacin, rifampicin, tetracycline, and fosfomycin, respectively).

Figure 8:
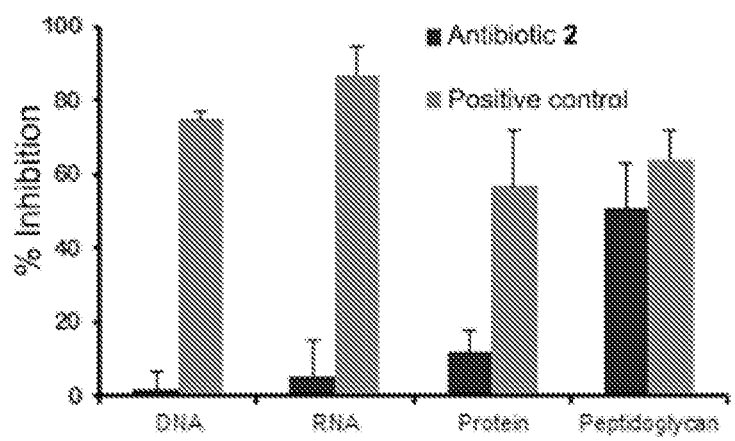
FIG. 8. Determination of the mechanism of action for quinazolinone 2. Macromolecular synthesis assays. Antibiotic 2 at 1 µg/mL, equivalent to ½ the MIC. Positive controls for DNA, RNA, protein, and peptidoglycan synthesis are ciprofloxacin (0.5 µg/mL), rifampicin (8 ng/mL), tetracycline (31 ng/mL), and fosfomycin (16 µg/mL), respectively.

As per our design paradigm, antibiotic 2 showed notable inhibition of cell-wall biosynthesis in these assays (51±12% compared to 64±8% for fosfomycin) and did not significantly affect replication, transcription, or translation (FIG. 8). To further confirm these results, additional in vitro transcription and translation assays were performed using a T7 transcription kit and an *E. coli* S30 extract system coupled with a β-galactosidase assay system, respectively. Compound 2 did not show any inhibition of either transcription or translation using these in vitro assays (FIG. 5).

Having demonstrated that biosynthesis of cell wall is attenuated by antibiotic 2, we next explored if it would inhibit purified recombinant PBP2a—the important cell-wall DD-transpeptidase in MRSA—by a competition assay with Bocillin FL, a fluorescent penicillin reporter reagent. This inhibition assay for PBPs has the limitation in that Bocillin FL is a covalent modifier of the active site of PBPs and the equilibrium is inexorably in favor of the irreversible acylation of the active-site serine by the reporter molecule. As such, the degree of inhibition by the non-covalent inhibitor (e.g., 2) will be underestimated. This is what was seen. Antibiotic 2 was able to inhibit Bocillin FL labeling of the active site of PBP2a in a competitive and dose-dependent manner, with an apparent $IC_{50}$ of 140±24 µg/mL, consistent with our design paradigm for binding of 2 at the active site (FIG. 9).

We have observed activity for quinazolinone 2 in strains of *S. aureus* that do not express PBP2a (Table 2.1), which indicates that the antibiotic is likely to bind to other PBPs as well. This is akin to the case of β-lactam antibiotics, which bind to multiple PBPs due to high structural similarity at the active sites. To demonstrate the ability to bind to other PBPs, membrane preparations of *S. aureus* ATCC 29213 (an MSSA strain) were used to assess broader PBP inhibition by antibiotic 2. Inhibition of PBP1 was observed, with an apparent $IC_{50}$ of 78±23 µg/mL (FIG. 10). Inhibition of PBP1 of *S. aureus* accounts for the antibacterial activity of meropenem, a carbapenem antibiotic. Because of the low-copy numbers of PBP2a in the membranes from MRSA, we could not demonstrate PBP2a inhibition in the membrane preparations directly. Inhibition of these PBPs by antibiotic 2 in living bacteria is expected to be more potent than what the Bocillin FL assay could evaluate, for the mechanistic reason that we described above.

As the quinazolinone class of antibiotics was discovered by in silico docking and scoring of compounds into the X-ray structure of PBP2a, we sought to determine the X-ray structure for the complex of quinazolinone 2 and PBP2a to validate the design paradigms. Soaking experiments of PBP2a crystals with 2 resulted in a structure at 1.95-Å resolution for the complex. This structure revealed density for antibiotic 2 bound to the allosteric site of PBP2a at 60-Å distance from the DD-transpeptidase active site (FIG. 7a). The critical binding of ligands such as the nascent cell-wall peptidoglycan at the allosteric site leads to the opening of the active site, enabling catalysis by PBP2a.

The structure revealed alterations of spatial positions of certain residues (Lys406, Lys597, Ser598, Glu602, and Met641) within the active site of the complex, consistent with occupation by an antibiotic molecule, but density for it was not observed. However, we cannot rule out that these alternative active-site conformations could not have come about due to the allosteric conformational change. This observation, along with the earlier kinetic measurements exhibiting competition between Bocillin FL and 2, indicated that the antibiotic binds to the active site; however, the additional binding at the allosteric site was unanticipated.

Determination of the binding affinity at the allosteric site was performed using intrinsic fluorescence quenching of purified PBP2a, which had been modified covalently within the active site by the antibiotic oxacillin. Hence, compound 2 would be expected to bind only to the allosteric site. A $K_d$ of 6.8±2 µg/mL was determined (FIG. 11). Therefore, we have evidence for binding of the antibiotic 2 to the allosteric site (X-ray) and to the active site (kinetic assays for competitive inhibition and X-ray altered conformations for the active-site residues) of PBP2a. Binding of antibiotic 2 at the allosteric site induces conformational changes at the active site (FIG. 7b). All of these movements serve to double the area and volume of the active site.

In summary, we have described a novel class of antibiotics that exhibit excellent in vitro and in vivo activity against *S. aureus*, and its problematic kin MRSA and its resistant variants. In inhibition of PBP2a of MRSA, antibiotic 2 binds to both the allosteric and to the catalytic sites, a duality that works in concert in incapacitating this important enzyme. β-Lactam antibiotics—penicillins, cephalosporins, carbapenems, etc.—are known inhibitors of PBPs, which are essential enzymes in cell-wall biosynthesis. Resistance to β-lactam antibiotics is widespread among pathogens, and in the case of MRSA, it encompasses essentially all commercially available drugs (Fisher et al., *Chem. Rev.* 105, 395-424 (2005); Llarrull et al., *Curr. Opin. Microbiol.* 13, 551-7 (2010)). In light of the fact that quinazolinones are non-β-lactam in nature, they circumvent the known mechanisms of resistance to β-lactam antibiotics. As such, they can be used against MRSA, a clinical scourge that kills approximately 20,000 individuals annually in the US alone.

In Silico Screening.

A library of 1.2 million drug-like compounds from the ChemDiv subset of the ZINC database was prepared for high-throughput virtual screening against the X-ray structure of PBP2a (PDB ID: 1VQQ). The top scoring 10% of the compounds were cross-docked with Glide-SP, Autodock, Gold-chemscore, Gold-goldscore, and Gold-PLP. The top scoring 2,000 poses from each were extracted and refined using Glide-XP mode. Finally, the best 2,500 were clustered according to structural similarity using hierarchical clustering. From these, 118 compounds were selected for in vitro activity experiments.

MIC Determination.

MICs were evaluated following the CLSI microdilution method in BBL™ Mueller-Hinton II broth (Wikler et al., *Clinical Laboratory Standards Institute Document M7-A7*, 29 (2009)). Strains tested are listed in Table 2.1. Briefly, two-fold serial dilutions of compound were prepared in triplicate in 96-well plates and inoculated with $5 \times 10^5$ cfu/mL of the bacterial suspension. Plates were incubated at 37° C. for 16-20 hours.

Compound Synthesis.

Antibiotic 2 was synthesized and characterized as detailed in the Example 1 above.

Cytotoxicity.

HepG2 cells (ATCC HB-8065) were maintained in monolayer culture at 37° C. and 5% $CO_2$ in Dulbecco's Modified Eagle's Medium supplemented with 10% fetal bovine serum, non-essential amino acids, 2 mM L-glutamine, and 1% penicillin-streptomycin. After overnight incubation, the cells were treated with compound 2 for 16 hours at concentrations from 2 µg/mL to 128 µg/mL. The cells were washed with Dulbecco's PBS twice, 150 µL of XTT working solution was added to each well, followed by 3-h incubation. Absorbance at 475 nm (test wavelength) and 660 nm (reference wavelength) was read with a microplate reader. Experiments were performed in triplicate and repeated twice. $IC_{50}$ values were calculated using GraphPad prism 5.

Hemolysis.

Fresh heparinized human blood was washed three times by centrifugation at 1,200 g for 10 min in 100 mM PBS, pH 7.4. A 10% red-blood cell (RBC) suspension was prepared in PBS. Antibiotic 2 at 0.5, 5, and 50 µg/mL was added to aliquots of the 10% RBC suspension and incubated at 37° C. A positive control of 0.2% Triton was used. Samples were centrifuged at 1,200 g for 10 min and the supernatant measured for absorbance at 541 nm.

Plasma Stability.

Compound 2 (20 µM) was incubated in blank mouse plasma at 37° C. and aliquots were taken at specific time points and quenched with two volumes of acetonitrile containing internal standard. Samples were centrifuged and analyzed by reverse-phase UPLC.

Microsomal Stability.

Compound 2 (2 µM) was incubated with pooled rat or human S9 (1 mg/mL), containing 1 mM NADPH and 3.3 mM $MgCl_2$ in 100 mM potassium phosphate buffer, pH 7.4 at 37° C. Aliquots were taken at 0, 5, 10, 20, 30, 40, and 60 min, and mixed with two volumes of acetonitrile containing internal standard. The precipitated protein was centrifuged at 20,000 g for 15 min, and the supernatant was analyzed by reversed-phase UPLC.

Macromolecular Synthesis Assays.

The incorporation of radiolabeled precursors-[methyl-$^3$H]-thymidine, [5-$^3$H]-uridine, L-[4,5-$^3$H]-leucine, or D-[2,3-$^3$H]-alanine-into DNA, RNA, protein, or peptidoglycan, respectively, in logarithmically growing *S. aureus* (ATCC 29213) was measured using a previously published method, with aliquots taken every 20 min over a 120-min incubation period (Wilson et al., *Antimicrob. Agents Chemother.* 39, 1925-33 (1995)). Known antibiotics for each pathway were used as positive controls: ciprofloxacin (0.5 µg/mL), rifampicin (8 ng/mL), tetracycline (31.25 ng/mL), and fosfomycin (16 µg/mL), respectively.

In Vitro Transcription and Translation Assays.

For in vitro translation, the *E. coli* S30 Extract System for Circular DNA was used to set up the reactions using plasmid pCP 19 containing the lacZ gene for β-galactosidase. Reaction mixtures were supplemented with two-fold dilutions of antibiotic 2 and the β-Galactosidase Enzyme Assay System with Reporter Lysis Buffer was used to quantify the amount of β-galactosidase translated by measuring absorbance at 420 nm. For in vitro transcription, a TranscriptAid T7 High Yield Transcription kit was used with a pET24a/dacB DNA construct under the T7 promoter. The purified plasmid was linearized using the restriction endonuclease XhoI and then purified according to the manufacturer's instructions. A series of samples were prepared and supplemented with two-fold dilutions of antibiotic 2. Samples were analyzed by running on a denaturing 1% formaldehyde agarose gel and stained with ethidium bromide to visualize RNA. Intensities of the bands were quantified and compared to the control to determine the amount of transcription occurring in the presence of 2.

Membrane Isolation.

*S. aureus* (ATCC 29213), a methicillin-sensitive strain, was grown in Difco Luria-Bertani (LB) broth at 37° C. until an $OD_{625}\sim0.8$. Cells were centrifuged at 3,200 g for 30 min at 4° C. and washed once with cold 100 mM $NaH_2PO_4$, 50 mM $NaHCO_3$, pH 7.5, buffer. The cells were resuspended in 10 mL cold buffer containing complete EDTA-free protease inhibitor, 200 µg/mL lysostaphin, 15 µg/mL DNase I, 10 mM $MgCl_2$, and 1 mM EDTA and incubated for 30 min at 37° C. Cells were sonicated using a Branson Sonifer for 5×1 min cycles, with 2 min of rest in between each cycle, and the lysate was centrifuged at 3,200 g for 20 min at 4° C. The supernatant was then ultracentrifuged at 32,000 rpm for 1 h at 4° C. and the pellet was washed once with cold buffer. The resulting membrane was resuspended in buffer, quantified using the BCA Protein Assay Kit, and the concentration was adjusted to 9 mg/mL.

Bocillin FL PBP Binding Assays.

The Bocillin FL competition assays were performed with purified PBP2a and membrane extracts. PBP2a was purified using a previously described protocol (Fuda et al., *J. Biol. Chem.* 279, 40802-40806 (2004)). For purified PBP2a, 1 μM protein in 25 mM HEPES, pH 7, 1 M NaCl buffer was incubated at 37° C. in the presence of varying concentrations of compound 2 for 10 min. For membrane extracts, 150 μg of the extract in 100 mM $NaH_2PO_4$, pH 7.5, 50 mM $NaHCO_3$ was incubated at 37° C. for 10 min in the presence of varying concentrations of compound 2. Bocillin FL (20 μM for purified protein and 30 μM for membranes) was added and the reactions were incubated a further 10 min, then quenched by the addition of laemmli sample buffer (2× stock solution) and boiling for 5 min. Samples were centrifuged, loaded to SDS-PAGE, the gels were visualized immediately using a Storm840 Scanner, and fluorescence was quantified using ImageQuant software. $IC_{50}$ values were calculated using GraphPad prism 5, using the previously published equation.

Animals.

Mice (ICR female, 6-8 weeks old, 17-20 g body weight) were maintained on a 12:12 light/dark cycle at 72±2° F. and provided with Teklad 2019 Extruded Rodent Diet and water ad libitum. All procedures were performed in accordance with the University of Notre Dame Institutional Animal Care and Use Committee.

In Vivo Efficacy.

Groups (n=6/group) of mice were infected with MRSA (0.5 mL of ATCC 27660 at a final concentration of $5×10^7$ CFU/mL in 5% porcine mucin) intraperitoneally (ip). Following infection, mice were given iv doses by tail vein injection of compound 2, vancomycin (5 mg/kg, positive control), or vehicle at 30 min and 4.5 h after infection. The number of surviving mice was monitored for 48 h. The negative control (vehicle) typically results in the death of all mice. Quinazolinone 2 was dissolved in saline, sterile-filtered, and administered at doses of 2.5, 5, 7.5, 10, 20, and 30 mg/kg. The $ED_{50}$ value was calculated using GraphPad prism 5.

Pharmacokinetics (PK) Studies.

A single dose of compound 2 was administered to mice (n=3 per time point) by tail vein injection or by oral gavage at 10 mg/kg. Blood was collected by cardiac puncture in heparinized syringes at 2, 5, 20, and 40 min and at 1, 2, 3, 4, 8, 18, and 24 h after iv dosing and at 0.5, 1, 2, 3, 4, 6, 9, 24, and 30 h after po dosing. Blood was centrifuged to obtain plasma. A 50-μL aliquot of plasma was mixed with 100 μL of acetonitrile containing internal standard (5 μM final concentration), followed by centrifugation at 20,000 g for 15 min. The supernatant was analyzed by reverse-phase UPLC. PK parameters were calculated as described in the Plasma protein binding and Pharmacokinetics sections below (see also Gooyit et al. *J. Med. Chem.* 54, 6676-6690 (2011)).

Structural Determination of the PBP2a:2 Complex.

Wild-type PBP2a crystals were grown following the procedure previously published. Wild-type PBP2a crystals were soaked in the precipitation solution containing 1 mM antibiotic 2 for 24 h at 4° C. Crystals were then soaked briefly in a cryo-protectant (70:30 v/v mixture of paratone/paraffin oil) prior to flash cooling at 100K. Diffraction data sets were collected at synchrotron beamline PX1 at the SLS facility (Switzerland) at 0.9999 Å wavelength. Data sets resulting from three separate soaking experiments were merged and then solved by molecular replacement and refined as detailed in the Structure determination and refinement section below. The crystallographic statistics for the resulting 1.95-Å resolution complex were recorded, and the PDB ID for the deposited coordinates is 4CJN.

Strains.

*Staphylococcus aureus* strains NRS70 (also designated N315), NRS123 (also designated MW2, C1999000459, USA400, and 99065), NRS128 (also designated NCTC8325 and RN0031), NRS100 (also designated COL), NRS119 (also designated SA LinR #12), NRS120 (also designated SA LinR #13), VRS1 (also designated HIP 11714), VRS2 (also designated HIP 11983) were obtained through the Network on Antimicrobial Resistance in *Staphylococcus aureus* (NARSA). *S. aureus* strains ATCC 29213, ATCC 27660, MRSA252 (ATCC BAA-1720), *S. epidermidis* ATCC 35547, *S. haemolyticus* ATCC 29970, *E. faecium* NCTC 7171 (ATCC 19734), *K. pneumoniae* ATCC 700603, *A. baumannii* ATCC 17961, *P. aeruginosa* ATCC 27853, *E. aerogenes* ATCC 35029) and *E. coli* ATCC 25922 were purchased from the American Type Culture Collection (ATCC).

Plasma Protein Binding.

Plasma was centrifuged at 1,200 g and 200 μL and was added to the sample chamber of a rapid equilibrium dialysis device, and 350 μL 0.1 M PBS, pH 7.4 supplemented with 0.15 mM NaCl was added to the adjacent chamber. Antibiotic 2 was added to the sample chambers to a final concentration of 10 μM and dialyzed in an orbital shaker for 6 h at 37° C. Aliquots from both chambers were quenched with 1:2 v/v acetonitrile containing an internal standard. The samples were concentrated to dryness on a miVac concentrator and the residue resuspended in 50:50 acetonitrile/water. Samples were analyzed by reverse-phase ultraperformance liquid chromatography (UPLC) with UV/Vis detection. Plasma protein binding of quinazolinone 2 was 98.0±0.04% in mice and 96.5±0.70% in humans.

UPLC Analysis.

A Waters Acquity UPLC system was used, which was equipped with a binary solvent manager, an autosampler, a column heater, and a photodiode array detector. The chromatographic conditions consisted of elution at 0.4 mL/min with 10% acetonitrile/90% water for 2 min, followed by a 10-min linear gradient to 80% acetonitrile/20% water, and a 3-min linear gradient to 100% acetonitrile and UV/Vis detection at 290 nm. The column used was an Acquity UPLC HSS C18 1.8 μm, 2.1×100 mm.

Pharmacokinetic Parameters.

The area under the concentration-time curve up to the last quantifiable sampling time ($AUC_{0-last}$) was calculated by the trapezoidal rule. $AUC_{0-\infty}$ was calculated as $AUC_{0-last}+(C_{last}/k)$, where $C_{last}$ is the concentration at the last quantifiable sampling time and k is the elimination rate constant. The concentration at time=0 ($C_0$) was estimated from the first sampling times by back-extrapolation using log-linear regression analysis. Half-lives ($t_{1/2\alpha}$ and $t_{1/2\beta}$) were estimated from the linear portion of the initial or terminal concentration-time data by linear regression, where the slope of the line was the rate constant k and $t_{1/2\alpha}=\ln 2/k$. Volume of distribution (Vd) was calculated as the dose divided by the initial concentration ($C_0$). Clearance (CL) was calculated from the dose divided by $AUC_{0-\infty}$. Oral bioavailability (F) was calculated by dividing the $AUC_{po}$ by the $AUC_{iv}$, as equivalent iv and po doses were administered.

Pharmacokinetics.

After a single 10 mg/kg iv dose of 2 (FIG. 3), the compound distributed rapidly to tissues with a distribution $t_{1/2\alpha}$ of 14.6 min and a volume of distribution Vd of 0.3 L/kg (Table 2.2). Plasma levels of 2 were sustained above MIC for 2 h and declined slowly to 0.142±0.053 μg/mL at 24 h, with a long elimination half-life of 22.3 h. Systemic exposure, as measured by $AUC_{0-\infty}$, was 1410 μg·min/mL. The compound had low clearance of 7.07 mL/min/kg, less than 10% of hepatic blood flow in mice. After a single 10 mg/kg oral (po) dose of 2, the compound was absorbed quickly, with a $t_{1/2absorption}$ of 25 min. Maximum concentrations of 1.29 μg/mL were achieved at 1 h. Systemic exposure was 932 μg·min/mL. The compound distributed to tissues with a half-life of 2.06 h. The terminal half-life was long (58.2 h) and the absolute oral bioavailability was 66%.

Structure Determination and Refinement.

Diffraction data sets were processed using XDS, scaled with SCALA from the CCP4 package, and the structure was solved by molecular replacement using PHASER with the PBP2a structure as the initial model (PDB ID: 1VQQ). The models were refined with several cycles using PHENIX and BUSTER. Water molecules were added with BUSTER. Ramachandran statistics are as follows: 97.03% residues in most favored regions, 2.50% residues in allowed regions, and 0.47% in disallowed regions.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method to increase the antibacterial effectiveness of a beta-lactam antibiotic comprising administering the beta-lactam antibiotic in combination, concurrently or sequentially, with a compound of Formula (V):

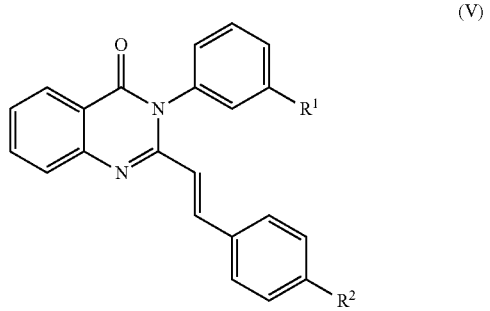

or a pharmaceutically acceptable salt or solvate thereof, wherein $R^1$ is hydroxy, acetoxy, —CO$_2$H, amino, —NH—C(=O)Me, —NH—C(=O)OMe, —NH—SO$_2$Me, —C(=O)NH$_2$, —C(=O)NH(C$_1$-C$_8$)alkyl-OH, —C(=O)NH(3-picolinyl), wherein the pyridine moiety of the picolinyl group is optionally substituted with alkyl or alkoxy, —NH(C$_1$-C$_8$)alkyl, or —CH$_2$NH—C(=O)Me, and $R^2$ is H, methyl, nitrile, or ethynyl; wherein the activity of the compound of Formula (V) and the beta-lactam antibiotic is synergistic.

2. The method of claim 1 wherein $R^1$ is hydroxy, —CO$_2$H, —NH—C(=O)Me, —NH—SO$_2$Me, —NH—C(=O)OMe, or —C(=O)N(H)CH$_2$CH$_2$OH.

3. The method of claim 2 wherein $R^2$ is nitrile, methyl, or ethynyl.

4. The method of claim 1 wherein the compound of Formula (V) has a minimum-inhibitory concentrations (MIC) against methicillin-resistant Staphylococcus aureus strains of less than 2.5 µg/mL.

5. The method of claim 4 wherein the ΔMIC in the presence of bovine serum albumin compared to the absence of the bovine serum albumin is less than or equal to 8 fold.

6. The method of claim 1 wherein the compound is:

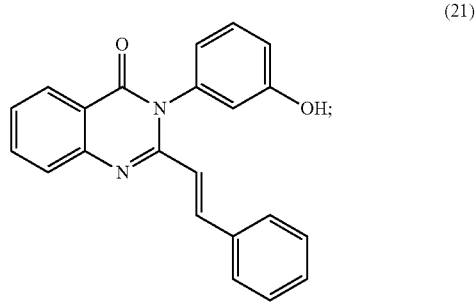

(21)

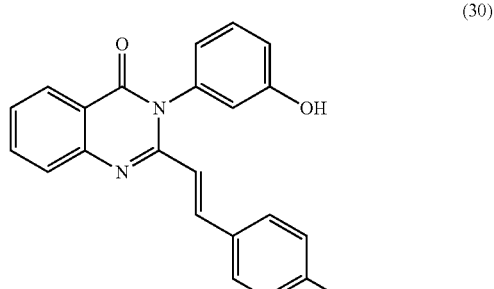

(30)

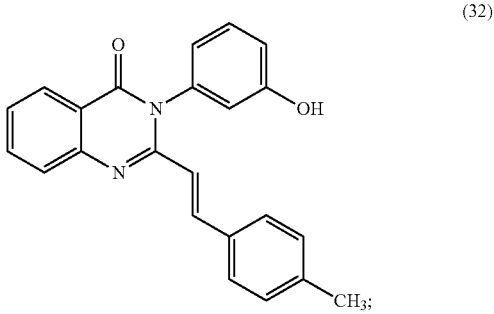

(32)

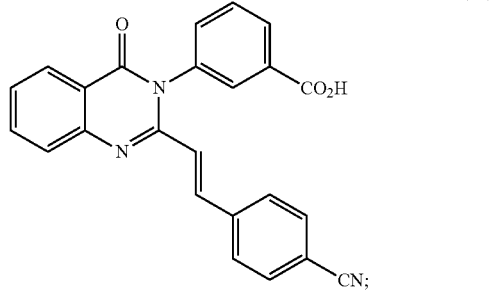

(36)

-continued
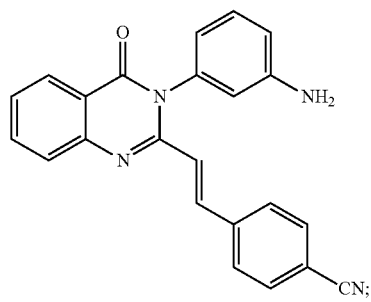 (37)
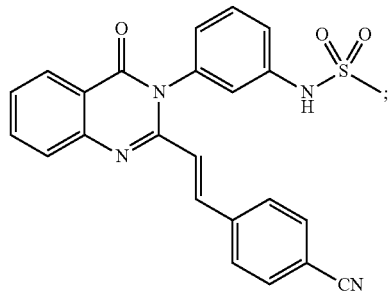 (38)
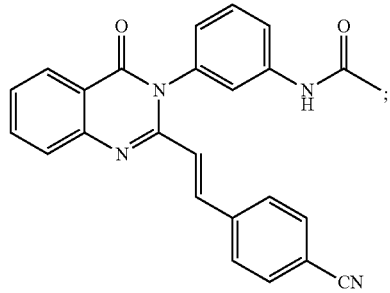 (39)
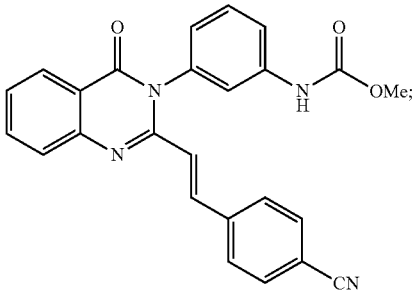 (40)
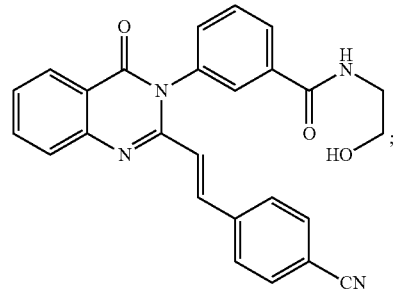 (52)
-continued
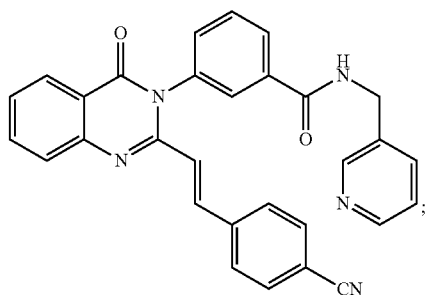 (53)
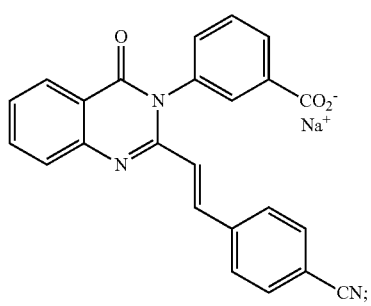 (57)
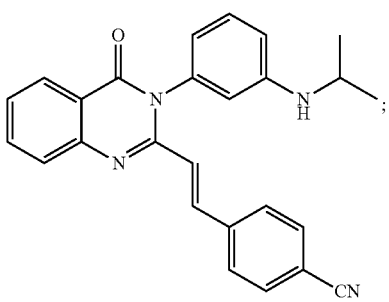 (63)
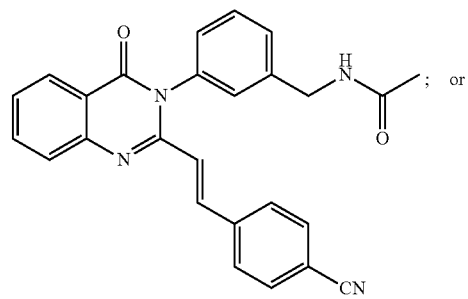 (65)
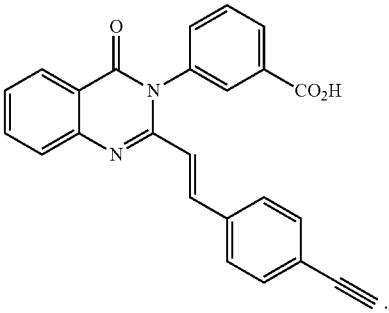 (70)

7. The method of claim 1 wherein the compound is:

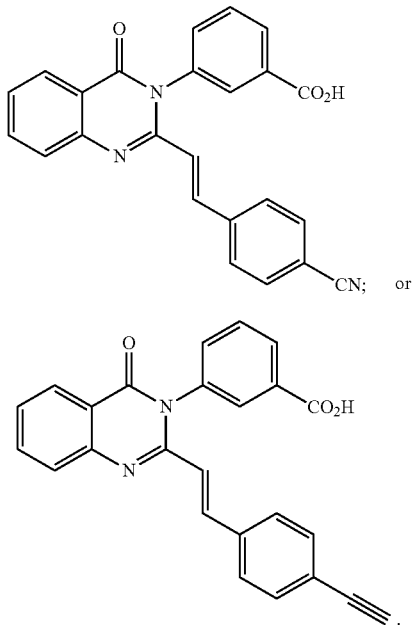

(36)

(70)

8. The method of claim 1 wherein the bacteria of the bacterial infection comprise gram negative bacteria.

9. The method of claim 1 wherein the bacteria of the bacterial infection comprise gram positive bacteria.

10. The method of claim 9 wherein the bacteria of the bacterial infection comprise at least one strain of *Enterococcus* or *Staphylococcus*.

11. The method of claim 1 wherein the beta-lactam antibiotic is amoxicillin, ampicillin, azlocillin, mezlocillin, apalcillin, hetacillin, bacampicillin, carbenicillin, sulbenicillin, ticarcillin, azlocillin, mecillinam, pivmecillinam, methicillin, ciclacillin, talampicillin, aspoxicillin, oxacillin, cloxacillin, dicloxacillin, flucloxacillin, nafcillin, pivampicillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, daptomycin, loracarbacef, latamoxef, penicillin, cefepime, aztreonam, carumonam; tigecycline, amikacin, gentamicin, kanamycin, neomycin, netilmicin, paromomycin, streptomycin, tobramycin, imipenem, biapenem, meropenem, ertapenem, faropenem, doripenem, panipenem, PZ-601, erythromycin, azithromycin, dirithromycin, telithromycin, clarithromycin, levofloxacin, ciprofloxacin, ofloxacin, gatifloxacin, norfloxacin, moxifloxacin, trovafloxacin, piperacillin, tazobactam, daptomycin, or ceftaroline.

12. The method of claim 11 wherein the beta-lactam antibiotic is a penem antibiotic or a carbapenem antibiotic.

13. The method of claim 12 wherein the penem antibiotic or carbapenem antibiotic is selected from the group consisting of biapenem, doripenem, ertapenem, faropenem, imipenem, meropenem, panipenem, and PZ-601.

* * * * *